US005522391A

United States Patent [19]

Beaudin et al.

[11] Patent Number: 5,522,391

[45] Date of Patent: Jun. 4, 1996

[54] DELAY GENERATOR FOR PHASED ARRAY ULTRASOUND BEAMFORMER

[75] Inventors: Raymond A. Beaudin, Andover; Michael P. Anthony, Chelmsford, both of Mass.

[73] Assignee: Hewlett-Packard Company, Palo Alto, Calif.

[21] Appl. No.: 287,971

[22] Filed: Aug. 9, 1994

[51] Int. Cl.[6] ........ A61B 8/00

[52] U.S. Cl. ........ 128/660.070

[58] Field of Search ........ 128/660.070, 661.010; 73/625–626

[56] References Cited

U.S. PATENT DOCUMENTS

| | | | |
|---|---|---|---|
| 4,173,007 | 10/1979 | McKeighen et al. | 367/11 |
| 4,227,417 | 10/1980 | Glenn | 73/625 |
| 4,232,380 | 11/1980 | Caron et al. | 367/88 |
| 4,445,186 | 4/1984 | Caron et al. | 364/521 |
| 4,688,045 | 8/1987 | Knudsen | 342/377 |
| 4,707,813 | 11/1987 | Moeller et al. | 367/103 |
| 4,870,971 | 10/1989 | Russell et al. | 128/661.01 |
| 4,949,259 | 8/1990 | Hunt et al. | 364/413.25 |
| 4,974,211 | 11/1990 | Corl | 367/7 |
| 5,111,695 | 5/1992 | Engeler et al. | 73/626 |
| 5,113,706 | 5/1992 | Pittaro | 73/626 |
| 5,261,281 | 11/1993 | Katakura et al. | 73/626 |
| 5,345,426 | 9/1994 | Lipschutz | 128/661.01 |
| 5,353,797 | 10/1994 | Matsushima et al. | 128/661.01 |

*Primary Examiner*—Francis Jaworski

[57] ABSTRACT

A delay generator for a beamformer in a phased array ultrasound imaging system is provided. The beamformer processes received signals from an array of transducer elements to form a receive beam. The beamformer includes a delay generator corresponding to each transducer element for delaying the received signal. The delay generator includes a delay unit and a delay controller. The delay is variable in response to a change delay signal supplied by the delay controller at discrete times during reception of ultrasound energy. According to one feature of the invention, the delay represents an exact solution, within the quantization error of the delay unit, to the delay equation for the delay at a given steering angle, transducer element and focal depth. According to another feature of the invention, the delay controller generates a change delay signal that steers the receive beam to a dynamically variable steering angle and dynamically focuses the receive beam during reception of ultrasound energy.

17 Claims, 15 Drawing Sheets

DELAY GENERATOR FOR PHASED ARRAY ULTRASOUND BEAMFORMER

FIELD OF THE INVENTION

This invention relates to ultrasound imaging systems which utilize phased array beam steering and focusing and, more particularly, to a delay generator for dynamically controlling focus in a receive beamformer.

BACKGROUND OF THE INVENTION

In a phased array ultrasound imaging system, an ultrasound transducer includes an array of N transducer elements. The system includes N parallel channels, each having a transmitter and a receiver connected to one of the transducer array elements. Each transmitter outputs an ultrasound pulse through the transducer element into an object being imaged, typically the human body. The transmitted ultrasound energy is steered and focused by applying appropriate delays to the pulses transmitted from each array element so that the transmitted energy adds constructively at a desired point. The transmitted ultrasound energy is partially reflected back to the transducer array by various structures and tissues in the body.

Steering and focusing of the received ultrasound energy are effected in a reverse manner. The reflected ultrasound energy from an object or structure arrives at the array elements at different times. The received signals are amplified and delayed in separate processing channels and then combined in a receive beamformer. The delay for each channel is selected such that the receive beam is steered at a desired angle and focused at a desired point. The delays may be varied dynamically so as to focus the beam at progressively increasing depths, or ranges, as the ultrasound energy is received. The transmitted beam is scanned over a region of the body, and the signals generated by the beamformer are processed to produce an image of the region.

In order to effect focusing and steering of the receive beam, delays must be applied to the received signals in each processing channel. The required delays vary with the steering angle of the receive beam, the position of each transducer element in the array, and with focal depth. Dynamic focusing is effected by varying the delays with time during reception of ultrasound echoes from progressively increasing depths. A typical phased array ultrasound transducer may include 128 elements or more. Thus, the computation and control of the required delay for each transducer element to effect dynamic focusing at a desired steering angle is difficult.

In one prior art approach, disclosed in U.S. Pat. No. 4,949,259 issued Aug. 14, 1990 to Hunt et al, the region being imaged is divided into zones at different depths from the transducer, and a delay is associated with each transducer element in each zone. This approach reduces the required number of delay coefficients compared to an ideal continuously-adjusted delay. However, since each delay is exactly correct at only one depth in the zone, the image quality is somewhat degraded.

U.S. Pat. No. 4,173,007, issued Oct. 30, 1979 to McKeighen et al., discloses an ultrasound imaging system using a memory with separate read and write capabilities to produce a dynamically variable delay. The delay can be varied by modifying the write or the read address pointer.

U.S. Pat. No. 5,111,695, issued May 12, 1992 to Engeler et al, discloses a method for dynamic phase focus of received energy for coherent imaging beam formation. The channel time delay is adjusted by apparatus with means for counting range clock signals, responsive to the initial steering angle, and a logic means for issuing fine time delay adjustment signals responsive to a phase control algorithm. Because of an approximation, the delays are not determined exactly.

Other prior art techniques for dynamic focusing are disclosed in U.S. Pat. No. 4,974,211 issued Nov. 27, 1990 to Corl; U.S. Pat. No. 5,113,706 issued May 19, 1992 to Pittaro; U.S. Pat. No. 4,870,971 issued Oct. 3, 1989 to Russell et al.; U.S. Pat. No. 4,707,813 issued Nov. 17, 1987 to Moeller et al.; and U.S. Pat. No. 4,227,417 issued Oct. 14, 1980 to Glenn.

SUMMARY OF THE INVENTION

According to the present invention, a delay generator for a beamformer in a phased array ultrasound imaging system is provided. The beamformer processes received signals from an array of transducer elements to form a receive beam. The beamformer includes a delay generator corresponding to each transducer element for delaying the received signal and a combiner for combining the delayed signals to form the receive beam. The delay generator comprises a delay unit for delaying the received signal, and a delay controller. The delay caused by the delay unit is variable in response to a change delay signal supplied by the delay controller at discrete times during reception of ultrasound energy to steer and dynamically focus the receive beam. Preferably, the delay controller includes means for generating the change delay signal in binary form such that an active state of the change delay signal causes the delay to change by one delay quantum.

According to one aspect of the invention, the change delay signal represents an exact solution, within the quantization error of the delay unit, to the equation for the delay at a given steering angle, transducer element and focal depth. The delay controller may include a plurality of registers for storing values representative of a delay curve for the selected steering angle and means for updating the registers at discrete times during reception of ultrasound energy. The change delay signal is generated each time the values in the registers meet a predetermined condition.

According to another aspect of the invention, the change delay signal represents a solution to the delay equation for the delay at a given transducer element to steer the receive beam to a dynamically variable steering angle and to dynamically focus the receive beam during reception of ultrasound energy. The delay controller may include a plurality of registers for storing values representative of a delay curve for steering the receive beam to the dynamically variable steering angle and for dynamically focusing the receive beam, and means for updating the registers at discrete times during reception of ultrasound energy. The change delay signal is generated each time the values in the registers meet a predetermined condition. In the preferred embodiment, the delay coefficients received by the delay controller contain information representative of a selected steering angle $\Theta$ and deviations $\Delta\Theta$ from the selected steering angle. The deviations $\Delta\Theta$ are specified for a predetermined number of zones in the region being imaged. The delay controller includes means for causing the receive beam to have a specified deviation $\Delta\Theta_Z$ from the selected steering angle $\Theta$ in each zone Z. This process is referred to below as "warping".

In one implementation, the delay generator is used in a digital beamformer, and the delay unit includes means for delaying digital representations of the received signals. In a second implementation, the delay generator is used in a continuous analog beamformer, and the delay unit includes means for delaying continuous analog representations of the received signals. In a third implementation, the delay generator is used in a discrete time analog beamformer, and the delay unit includes means for delaying sampled analog representations of the received signals.

BRIEF DESCRIPTION OF THE DRAWINGS

For a better understanding of the present invention, reference is made to the accompanying drawings which are incorporated herein by reference and in which:

FIGS. 11-1 and 11-2 show a block diagram of the hardware that is common to each group of eight channels in the delay generator with warping;

FIGS. 12-1 and 12-2 show a block diagram of the additional hardware that is added to the delay controller in each channel in the delay generator with warping; and FIGS. 13-1 and 13-2 show is a timing diagram that illustrates the calculation of deviation $\Delta\Theta$ in one zone in the delay generator with warping.

DETAILED DESCRIPTION

Figure 1:
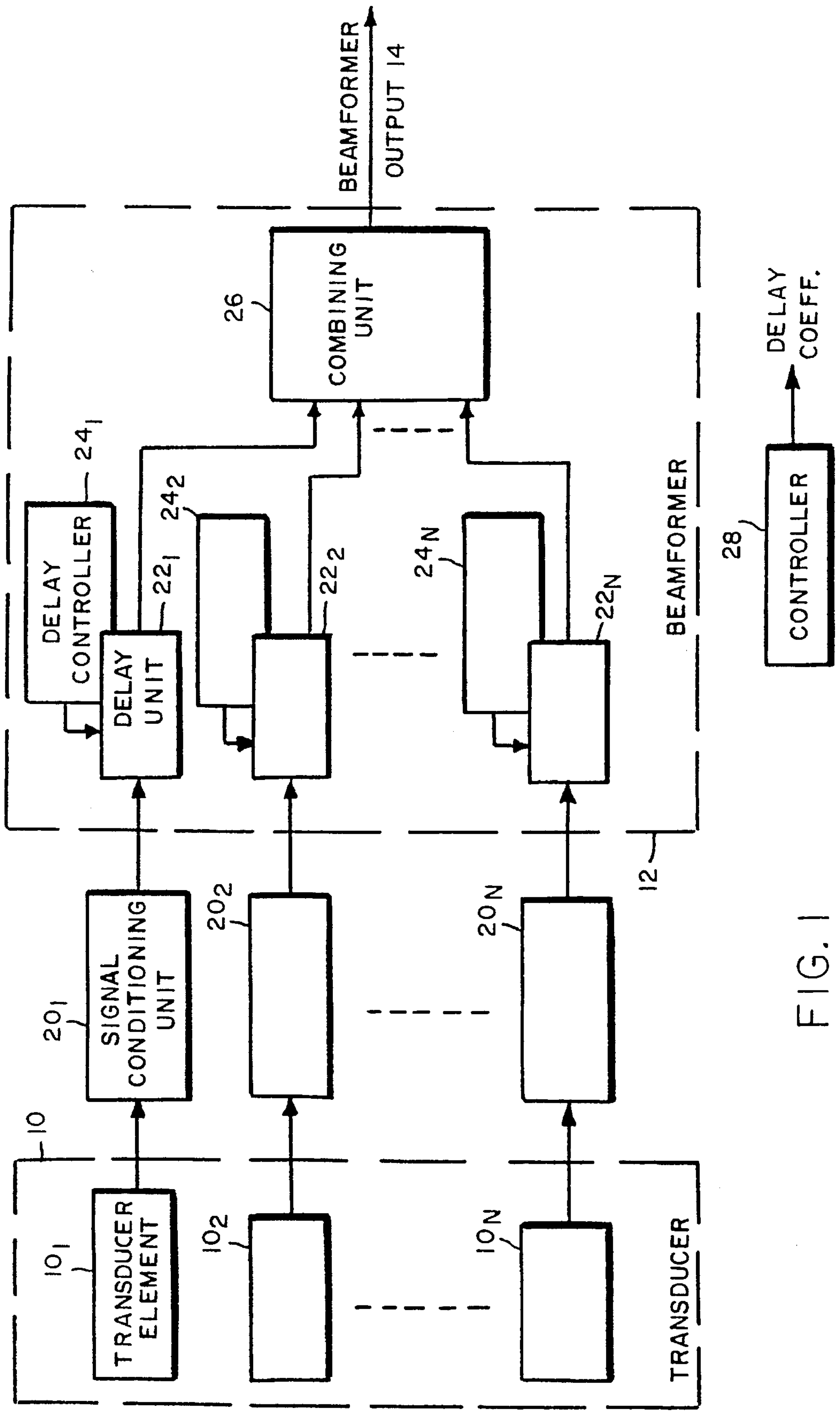
FIG. 1 is a block diagram of a phased array ultrasound beamformer.

A simplified block diagram of an ultrasound transducer array and a phased array ultrasound beamformer is shown in FIG. 1. The phased array ultrasound transducer 10 includes transducer elements $\mathbf{10}_1$, $\mathbf{10}_2$, . . . $\mathbf{10}_N$. The transducer elements are typically arranged in a linear or curvilinear array. The ultrasound transducer typically includes 128 transducer elements, but any number of transducer elements can be utilized.

The ultrasound transducer 10 transmits ultrasound energy into an object being imaged and receives reflected ultrasound energy. The transmitter portion of the ultrasound scanner is omitted from FIG. 1 for simplicity. By appropriately delaying the pulses applied to each transducer element, a focused ultrasound beam is transmitted into the object. The transmitted beam is focused and steered by varying the delays associated with each transducer element.

In a medical ultrasound imaging system, reflections, or echoes, are received from various structures and organs within a region of the human body. The reflected ultrasound energy from a given point within the patient's body is received by the transducer elements at different times. Each of the transducer elements $\mathbf{10}_1$, $\mathbf{10}_2$, . . . $\mathbf{10}_N$ converts the received ultrasound energy to an electrical signal. The electrical signals are conditioned by signal conditioning units $\mathbf{20}_1$, $\mathbf{20}_2$, . . . $\mathbf{20}_N$, and the conditioned signals are input to a beamformer 12. The beamformer 12 includes a separate processing channel for each transducer element. The beamformer 12 processes the electrical signals so as to control the receive sensitivity pattern and thereby effect focusing and steering of the received ultrasound energy. The depth and direction of the focal point relative to the ultrasound transducer 10 is varied dynamically with time by appropriately delaying the received signals from each of the transducer elements. The delayed signals are combined to provide a beamformer output 14.

The ultrasound transducer, the transmitter and the receive beamformer are parts of a phased array ultrasound scanner which transmits and receives ultrasound energy along a plurality of scan lines. Sector scan patterns, linear scan patterns and other scan patterns known to those skilled in the art can be utilized. The output 14 of the beamformer represents the received ultrasound energy along each scan line. The beamformer output 14 is processed according to known techniques to produce an ultrasound image of the region being scanned.

Respective electrical signals from the transducer elements $\mathbf{10}_1$, $\mathbf{10}_2$, . . . $\mathbf{10}_N$ are applied to individual processing channels of the beamformer 12. The beamformer 12 includes a delay unit $\mathbf{22}_i$ and a delay controller $\mathbf{24}_i$, where i varies from 1 to N, for each processing channel, and also includes a combining unit 26. The output of transducer element $\mathbf{10}_i$ is applied to the input of signal conditioning unit $\mathbf{20}_i$, and the output of signal conditioning unit $\mathbf{20}_i$ is applied to the input of delay unit $\mathbf{22}_i$. The outputs of delay units $\mathbf{22}_1$, $\mathbf{22}_2$, . . . $\mathbf{22}_N$ are applied to the inputs of combining unit 26. A controller 28 supplies delay coefficients and other control information to each processing channel.

Each signal conditioning unit $\mathbf{20}_i$ amplifies and filters the analog signal from the associated transducer element. Typically, the signal conditioning unit $\mathbf{20}_i$ also performs time gain control (TGC), as known in the art. The signal conditioning unit $\mathbf{20}_i$ may also perform digital or analog sampling of the analog signal. The delay unit $\mathbf{22}_i$ and the delay controller $\mathbf{24}_i$ form a delay generator which dynamically varies the delay in each channel as described in detail below. The combining unit may perform a simple summing of the delayed signals, weighting and summing of the delayed signals, or a more complex combining algorithm to provide the beamformer output 14.

Figure 2:
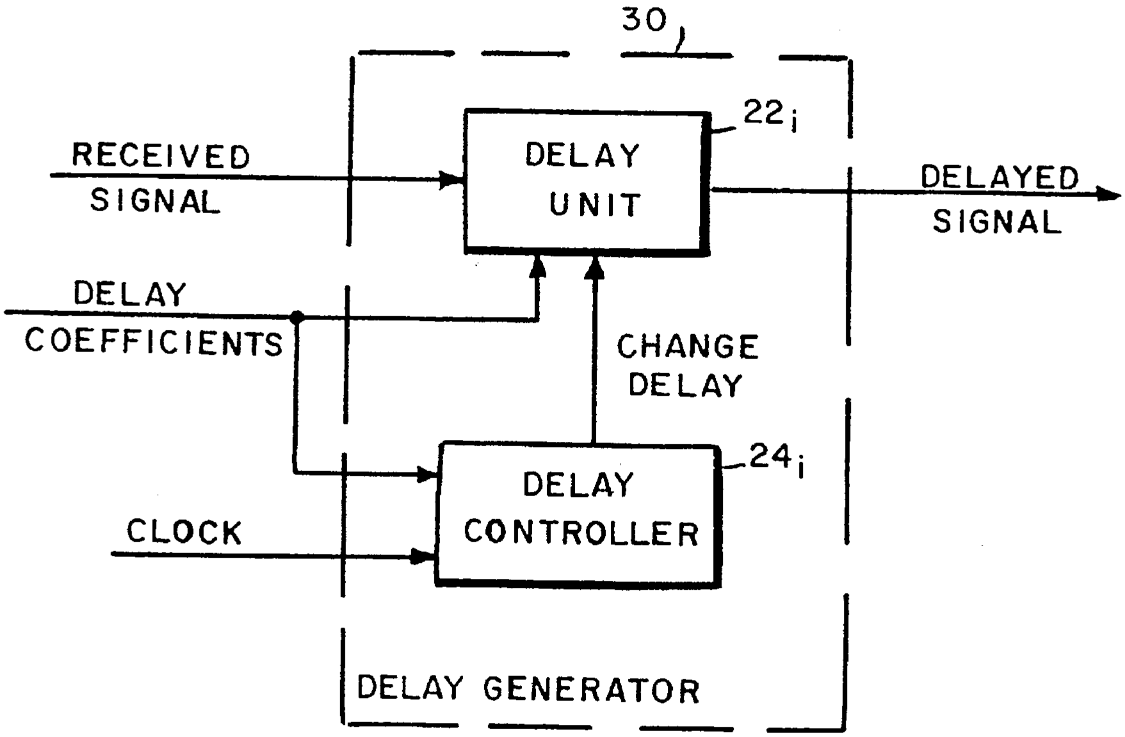
FIG. 2 is a simplified block diagram of the delay generator in accordance with the invention.

A simplified block diagram of a delay generator 30 in accordance with the invention is shown in FIG. 2. The delay generator 30 includes delay unit $\mathbf{22}_i$ for applying a required delay to the received signal and delay controller $\mathbf{24}_i$ for controlling the required delay. The delay controller $\mathbf{24}_i$ supplies a Change Delay signal to the delay unit $\mathbf{22}_i$. The received signal applied to the delay unit $\mathbf{22}_i$ can be a continuous analog signal, a sampled analog signal or a digital signal. Suitable delay units for each type of signal are described below. The delay controller $\mathbf{24}_i$ operates in a discrete time mode and supplies a binary Change Delay signal (change or no change) to the delay unit $22_i$ in synchronism with a clock.

The controller 28 (FIG. 1) supplies delay coefficients to the delay unit $22_i$ and to the delay controller $24_i$. The delay coefficients supplied to the delay unit $22_i$ represent the required initial delay for a particular transducer element to obtain the required steering angle of the receive beam. The initial delay may be specified for zero depth or for the shallowest depth of interest in the ultrasound image. The delay coefficients supplied to the delay controller $24_i$ represent the position of the transducer element in the array, typically referenced to the center of the array, the desired steering angle for the received beam and the time at which dynamic focusing is to start. It will be understood that different delay coefficients are supplied for each different steering angle.

During reception of ultrasound energy, the delay unit $22_i$ initially delays the received signal by the initial delay value. Thereafter, the delay controller $24_i$ operates in real time to determine the times when the delay must be changed in order to dynamically focus the receive beam. The Change Delay signals are supplied to the delay unit $22_i$ at discrete times so as to increment the delay applied by the delay unit $22_i$.

Figure 3:
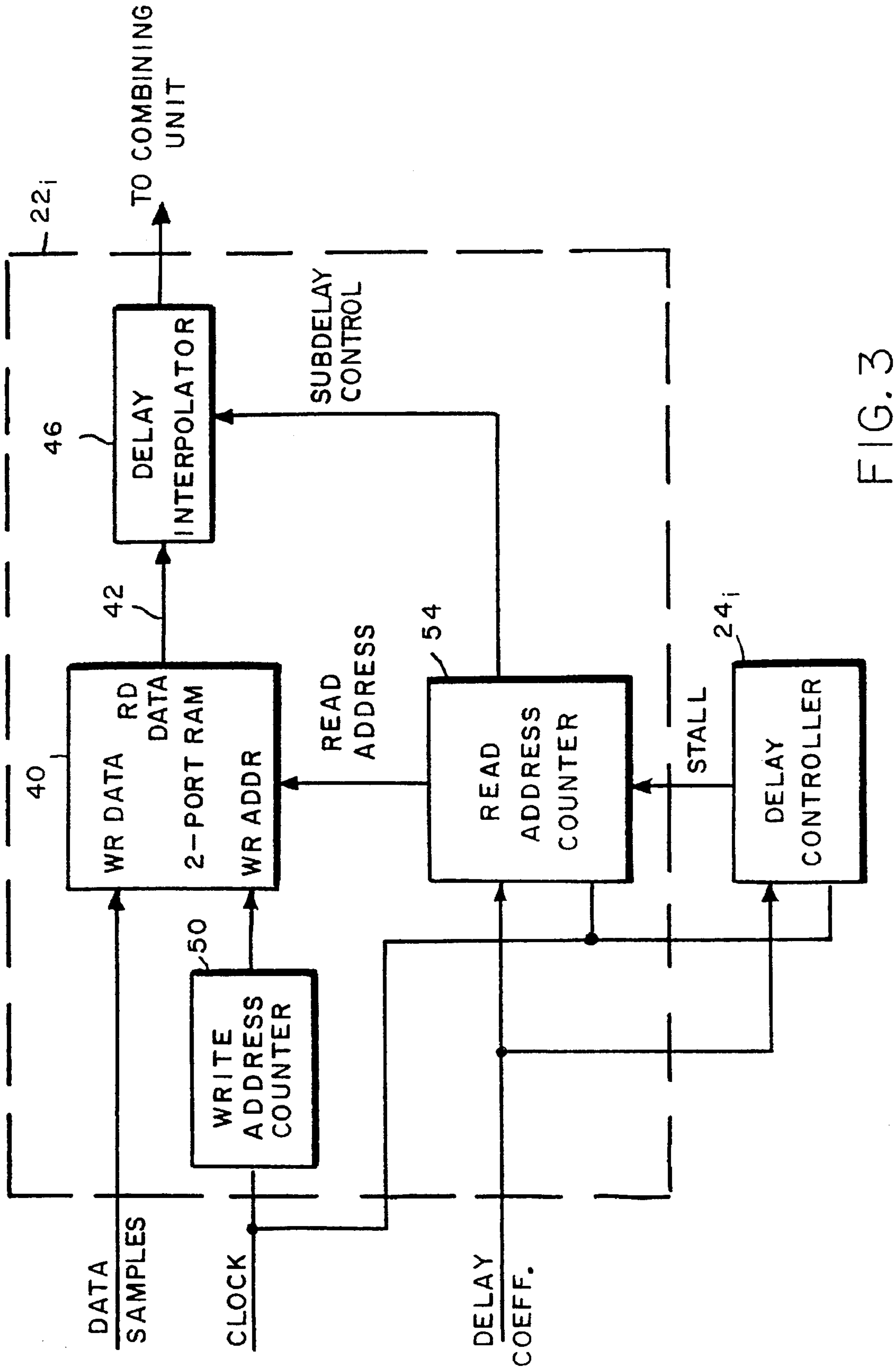
FIG. 3 is a block diagram of the delay generator for one processing channel of a digital ultrasound beamformer incorporating the present invention.

A block diagram of the delay unit $22_i$ and the delay controller $24_i$ for a digital ultrasound beamformer is shown in FIG. 3. The signal conditioning unit $20_i$ (FIG. 1) converts the received signal to a series of digital data samples. The data samples from the signal conditioning unit $20_i$ are input to a two port random access memory (RAM) 40, which permits simultaneous writing and reading of data. The two-port RAM 40 and associated circuitry delay each of the data samples by selected delays that are quantized in increments equal to the sampling-clock period. The delayed data samples are supplied on output 42 of two-port RAM 40 to a delay interpolator 46.

The two-port RAM 40 operates as a "circular" memory. Locations in the RAM 40 are sequentially addressed by a write address counter 50, and the data samples are written into the addressed locations. The data samples are delayed by reading data from addresses that are offset from the write addresses. The read addresses are sequenced to provide a continuous stream of output data that is delayed with respect to the input data. The delay in sampling-clock periods is equal to the number of memory locations between the read address and the write address.

In order to perform dynamic focusing during receive, the delay applied to the data samples must be varied dynamically. In the delay generator of FIG. 3, changes in delay are effected by changing the difference between the write address and the read address in two-port RAM 40. Typically, the required delay remains constant for several clock cycles and then is incremented by one clock cycle.

The read address for the two-port RAM 40 is supplied by a read address counter 54. Locations in the two-port RAM 40 are addressed by the read address counter 54, and the data samples stored in the addressed locations are supplied on read data output 42 to the delay interpolator 46. The required delay is established by the difference between the write address and the read address. During periods when the delay is constant, locations in the RAM 40 are sequentially addressed by read address counter 54 in synchronism with write address counter 50, with a fixed difference between the read address and the write address. When the delay is to be incremented by one clock cycle, the read address counter 54 is held constant (stalled) for one clock cycle. The stalling of the read address counter 54 effectively changes the difference between the write address and the read address, because the write address counter 50 is not stalled. The STALL signal in FIG. 3 thus corresponds to the Change Delay signal in FIG. 2.

STALL signals for the read address counter 54 are supplied by the delay controller $24_i$. The delay controller $24_i$ receives delay coefficients from the controller 28 as described above. The delay coefficients are also supplied to the read address counter 54 so as to preset the read address counter at an address which represents the required initial delay for the given transducer element and steering angle. The delay controller $24_i$ then controls the read address counter during reception of ultrasound energy by transducer array 10 in accordance with the delay equation, as described in detail below. During reception of ultrasound energy, the read address counter 54 is incremented by each clock pulse, except when a STALL signal is given by the delay controller $24_i$. When a STALL signal is given, the read address counter 54 is stalled for one clock cycle. Since the write address counter 50 advances on each clock cycle, the STALL signal effectively increases the delay applied to the data samples by one clock cycle.

Figure 6:
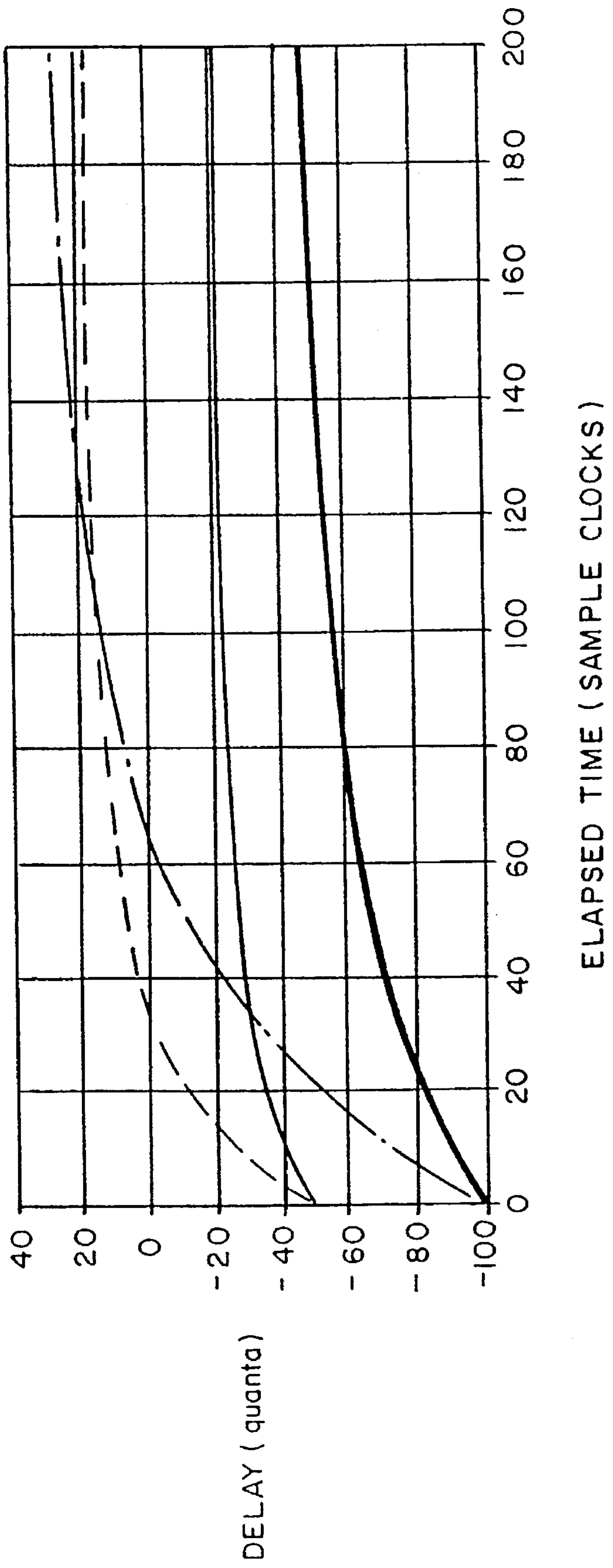
FIG. 6 is a graph of delay as a function of elapsed time for different transducer elements at a beam steering angle of 22.5°.

Examples of required delay as a function of elapsed time after transmission of an ultrasound pulse are shown in FIG. 6. The example shown in FIG. 6 illustrates the required delay for different transducer elements to achieve a steering angle of 22.5°. The read address counter 54 and the delay controller $24_i$ cause the RAM 40 to apply a delay which increases as a function of time as shown in FIG. 6. It will be understood that different delay curves are utilized, depending on the steering angle and the position of the transducer element in the array.

As noted above, the two-port RAM 40 delays the data samples by selected delays that are quantized in increments equal to one sampling-clock period. The output of RAM 40 is supplied to delay interpolator 46, which delays each data sample by a selected subdelay that is quantized in increments of less than the sampling period. Thus, for example, each sample in the data stream can be delayed by 0, $\frac{1}{4}\tau$, $\frac{1}{2}\tau$, or $\frac{3}{4}\tau$, where $\tau$ is the sampling period. The delay interpolator 46 permits generation of high quality images without increasing the sampling clock rate. The subdelay control information for delay interpolator 46 is received from read address counter 54. The delay interpolator 46 is preferably implemented as a finite impulse response (FIR) digital filter having different selectable delays that are quantized in delays less than the sampling period.

Figure 4:
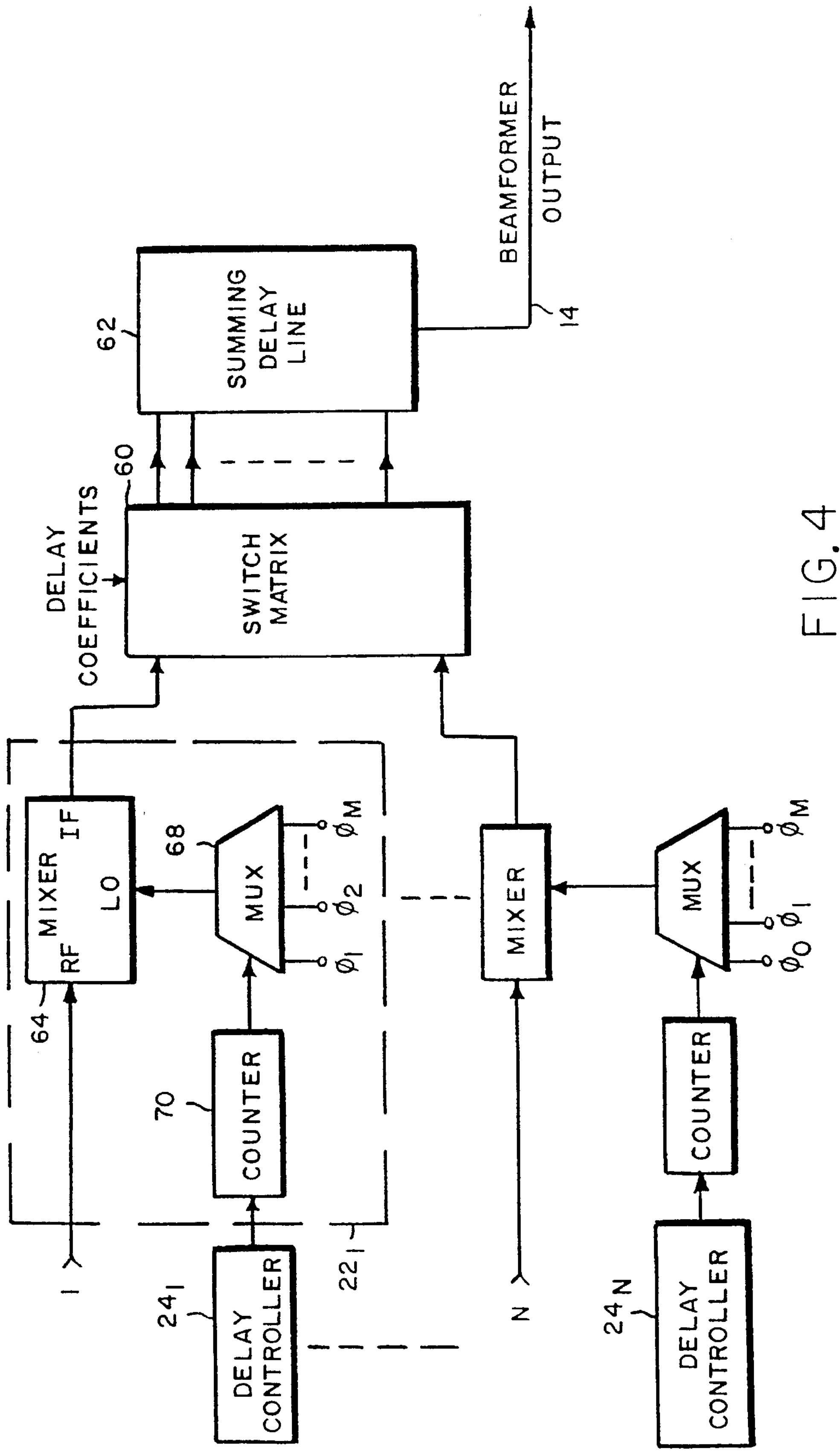
FIG. 4 is a block diagram of an analog ultrasound beamformer incorporating the delay generator of the present invention.

A block diagram of an analog beamformer incorporating a delay generator in accordance with the present invention is shown in FIG. 4. The architecture of FIG. 4 is based on the principles of U.S. Pat. No. 4,140,022 and employs a so-called mix and delay (i.e., fine delay added to coarse delay) mechanism for focusing and steering. In the beamformer of FIG. 4, the fine delay in each channel is provided by delay unit $22_i$ and delay controller $24_i$, and the coarse delay is provided by a switch matrix 60 and a summing delay line 62. The switch matrix 60 receives delay coefficients representative of the steering angle and focal depth and selects a tap on the summing delay line 62 for the received signal in each channel.

In the delay unit $22_i$, a mixer 64 is used to heterodyne selected clock phases $\Phi_1, \Phi_2, \ldots \Phi_M$ with the received signal. The selection of clock phases is controlled by a multiplexer 68, a counter 70 and the delay controller $24_i$. The multiplexer 68 selects one of the clock phases based on the state of counter 70. A delay coefficient loaded into the counter 70 represents a required initial delay to obtain a desired steering angle. The delay controller $\mathbf{24}_i$ then increments the counter 70 to maintain the required delay during reception of ultrasound energy. As described above, the delay controller $\mathbf{24}_i$ increments the counter 70 only when a change in delay is required.

Figure 5:
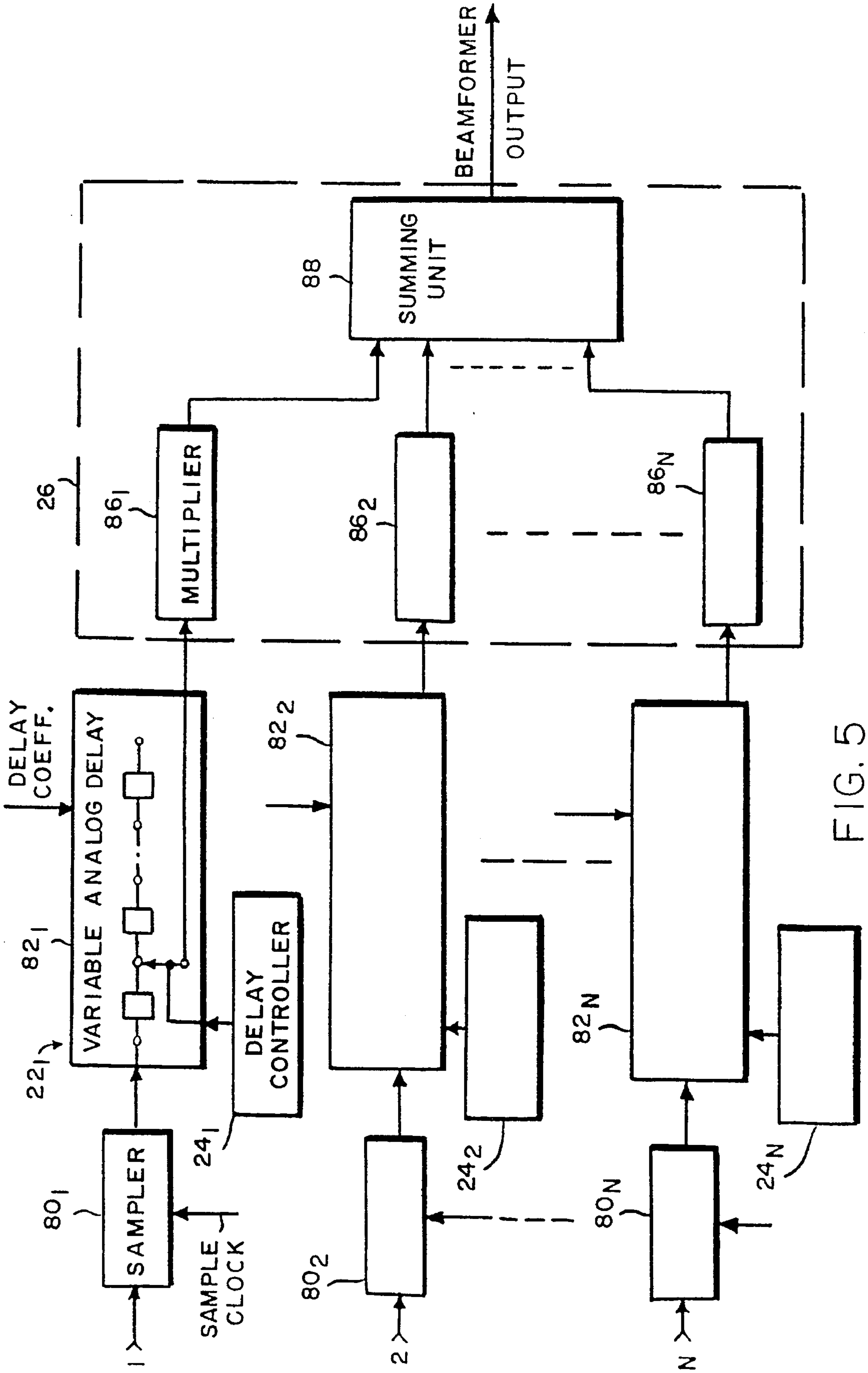
FIG. 5 is a block diagram of a discrete time analog ultrasound beamformer incorporating the delay generator of the present invention.

A third embodiment of a beamformer incorporating the delay generator in accordance with the present invention is shown in FIG. 5. The embodiment of FIG. 5 is a discrete time analog beamformer. The analog signal representative of the received ultrasound energy from each transducer element is sampled at discrete times by a sampler $\mathbf{80}_i$. The analog samples in each channel are input to a variable analog delay $\mathbf{82}_i$, which can be a charge coupled device (CCD), bucket brigade or other analog charge storage and transfer device. The variable analog delay $\mathbf{82}_i$ delays the analog samples such that the receive beam is dynamically focused along a line at a prescribed steering angle. The delay coefficients from controller 28 preset an initial delay value in the variable analog delay $\mathbf{82}_i$. The delay is then controlled during reception of ultrasound energy by the delay controller $\mathbf{24}_i$. Each time the delay must be incremented, the delay controller supplies a Change Delay signal to the variable analog delay $\mathbf{82}_i$ to increment the delay to the next value. The output of each variable analog delay $\mathbf{82}_i$ is input to the combining unit 26. In the embodiment of FIG. 5, the combining unit 26 is shown as including a multiplier $\mathbf{86}_i$ for each processing channel. The multipliers $\mathbf{86}_i$ adjust the signal level in each channel, typically for apodization and gain control. The outputs of multipliers $\mathbf{86}_i$ are input to a summing unit 88, which provides the beamformer output 14.

Figure 7:
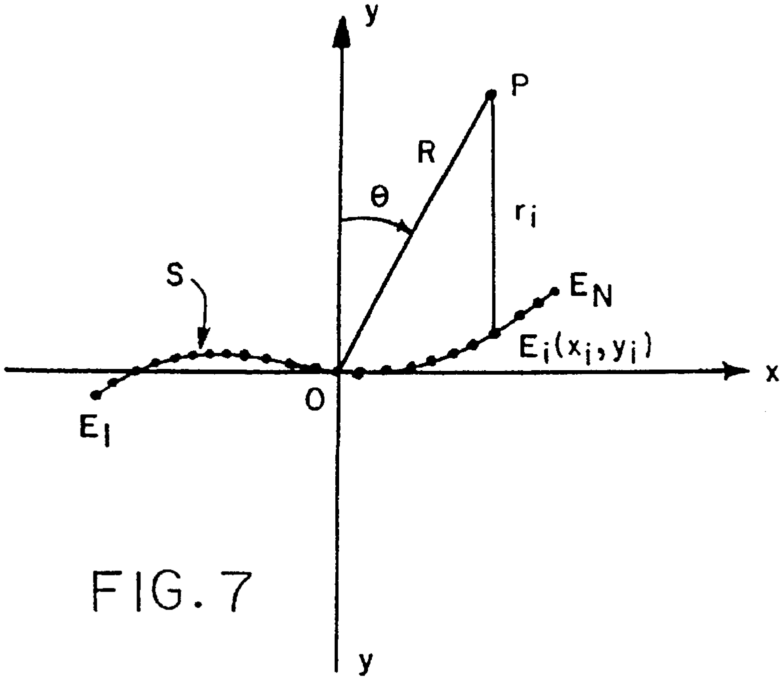
FIG. 7 is a graph that illustrates the geometry of a transducer array having an arbitrary shape.

In the beamformers described above, each sample of the received signal in a given channel is delayed in a delay unit $\mathbf{22}_i$ before being combined with signals from the other channels. The amount of delay for each channel must be controlled to produce a receive focus at a desired, time-varying point in the object. The ideal required delay can be derived from the imaging geometry as shown in FIG. 7. Given a finite sampling-clock period and a finite delay resolution (delay quantum), optimum beamformer performance requires that the delay applied to each sample be the nearest value to the ideal delay, chosen from the available discrete set of possible delay values. The function of the delay controller $\mathbf{24}_i$ is to control the delay unit $\mathbf{22}_i$ such that this optimum delay is achieved.

The delay unit $\mathbf{22}_i$ in the described beamformers maintains a constant delay until it receives a STALL signal from the delay controller $\mathbf{24}_i$. When the STALL signal is received, then the delay applied to the next sample is increased by one delay quantum. This new delay is maintained until the next STALL signal arrives. Thus the delay controller $\mathbf{24}_i$ must emit a STALL signal whenever the required delay for the next sample increases by one quantum.

Consider the geometry of FIG. 7. The coordinate system has its origin at point O on a multi-element transducer whose surface S may be of arbitrary shape. The transducer has N elements $E_1$ through $E_N$.

In order to produce a focus at point P, the round-trip propagation time for ultrasound energy from O to P to a transducer element $E_i$, plus the delay applied to the signal from that element, must be equal for all N elements, For the element at O, the round-trip propagation time is 2R/C (where C is the speed of sound in the object). We define the delay applied to the signal from this element to be zero for reference. Thus the following equation must be satisfied for each element $E_i$:

$$\frac{R}{C}+\frac{r_i}{C}+T_i=\frac{2R}{C} \tag{1}$$

where $T_i$ is the delay applied to the signal from the $i^{th}$ element.

Using the law of cosines, this condition can be expressed in terms of Θ, the steering angle with respect to a normal to the transducer, and the coordinates $(x_i, y_i)$ of element $E_i$ as:

$$T_i=\frac{R}{C}-\left[\left(\frac{R}{C}\right)^2-\frac{2R}{C^2}(x_i\sin\theta+y_i\cos\theta)+\frac{x_i^2+y_i^2}{C^2}\right]^{1/2} \tag{2}$$

We define $\tau_0$ to be the delay quantum and $T_0$ to be the sampling-clock period. We require $T_0=k\tau_0$, with k an integer $\geqq 1$. We can then re-express Equation (2) by taking $\tau_0$ as our unit of time.

With the following definitions:

t ≜ elapsed time since transmit, in units of $$T_0=\frac{2R}{CT_0}=\frac{2R}{kC\tau_0}$$

d ≜ delay required by (2) in units of $$\tau_0=\frac{T_i}{\tau_0}$$

S ≜ $(x_i \sin\theta+y_i \cos\theta)/C\tau_0$

X ≜ $(x_i^2+y_i^2)^{1/2}/C\tau_0$ we have:

$$d=\frac{kt}{2}-\left(\frac{k^2t^2}{4}-S\,kt+X^2\right)^{1/2} \tag{3}$$

where d, S, and X are understood to be the values applicable at a particular element $E_i$.

Equation (3) can be solved for t, giving:

$$t=\frac{1}{k}\ \frac{X^2-d^2}{S-d} \tag{4}$$

This equation can be understood as specifying, for the $i^{th}$ element, the elapsed time since transmit at which a given focal delay d is applicable. Equations (3) and (4) represent the ideal delay vs. elapsed-time function, in which both elapsed time and delay are continuous variables.

In the described beamformers, the delay value can be updated at each sampling-clock period. The delay controller $\mathbf{24}_i$ is required to decide, in each sampling-clock period, whether the applied delay value should be kept constant or be incremented by one unit of $\tau_0$ for the next sample. If an increment is required, the delay controller $\mathbf{24}_i$ must output a STALL signal. The algorithm for arriving at this discrete-time decision will now be derived from the continuous-time ideal-delay equations given above.

Figure 8:
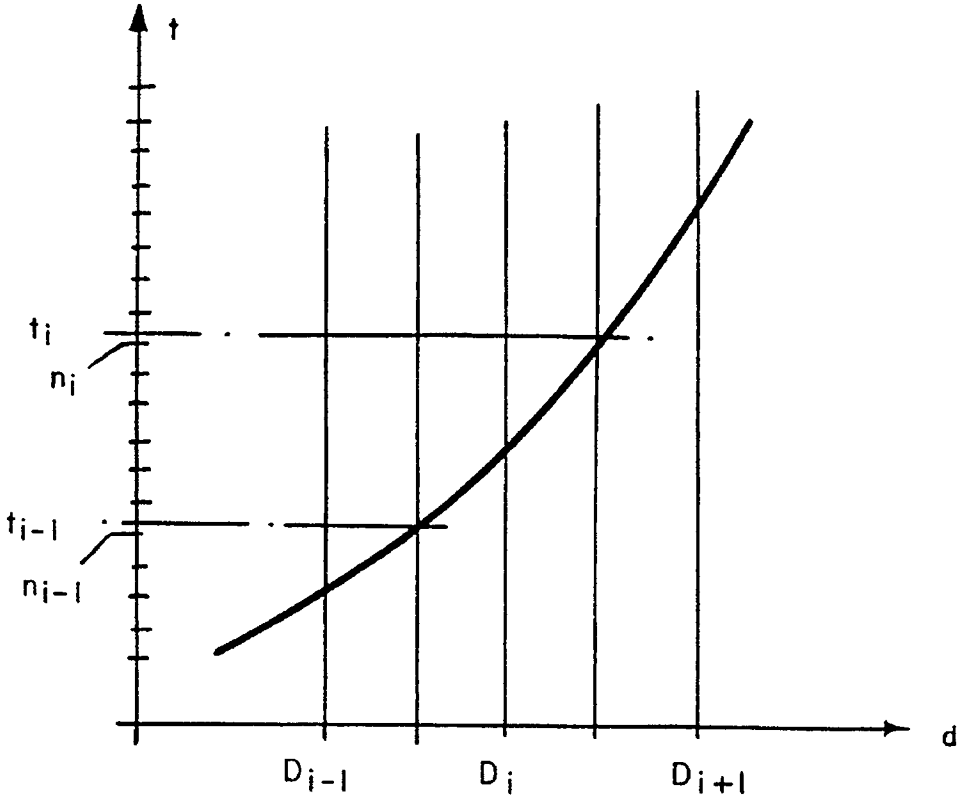
FIG. 8 is a graph of elapsed time as a function of delay, which illustrates the optimum discrete delay values.

In FIG. 8, Equation (4) is plotted for a small range of d. With reference to FIG. 8, we define:

a) the integer delay values $D_0, D_1, \ldots$ where $D_i=D_{i-1}+1$;

b) the elapsed time values (in general not integers) $t_0, t_1, \ldots$ where $t_i$ is the solution of Equation (4) at $d=D_i+½$; and c) the integer elapsed time values $n_0, n_1, \ldots$ where $n_i=GI\{t_i\}$ (i.e., $n_i$ is the Greatest Integer in $t_i$).

As can be seen from FIG. 8, the set of integer elapsed-time values for which $D_i$ is the nearest integer value to the ideal delay required by Equation (4) is $n_{i-1}+1 \ldots n_i$. Thus when n is equal to any $n_i$, the delay must increase by one quantum for the next sample (i.e., at these times the delay controller $\mathbf{24}_i$ must emit a STALL signal).

From the definitions above (see FIG. 8) it is apparent that:

$$n_i - n_{i-1} = GI\{t_i - n_{i-1}\} \quad (6a)$$

$$\text{and } t_i - n_i = FP\{t_i - n_{i-1}\} \quad (6b)$$

Where GI is defined above, the FP means "Fractional Part", i.e., FP{x}=x−GI{x}.

We can write (see FIG. 8):

$$t_i - n_{i-1} = (t_i - t_{i-1}) + (t_{i-1} - n_{i-1}) \quad (7)$$

From Equation (4) and the definitions above, it can be shown that the change in t resulting from a change in d from $(D_{i-1}+½)$ to $(D_i+½)$ is:

$$t_i - t_{i-1} = \frac{\left( t_{i-1} - \frac{2}{k}(D_{i-1}+1)\right.}{S - D_{i-1} - \frac{3}{2}} \quad (7a)$$

Substituting this result into Equation (7), and using the definition $D_i = D_{i-1}+1$, we obtain:

$$t_i - n_{i-1} = \frac{n_{i-1} - \frac{2}{k} D_i + (t_{i-1} - n_{i-1})\left(S - D_{i-1} - \frac{1}{2}\right)}{S - D_i - \frac{1}{2}} \quad (8)$$

In Equation (8), $t_i - n_{i-1}$ is obtained as the result of a division operation. This division can be carried out by repeatedly subtracting the denominator in Equation (8) from the numerator, until the residue of the numerator is less than the denominator. Then the number of such subtractions is equal to $GI\{t_i - n_{i-1}\}$, and therefore, by Equation (6a), to $n_i - n_{i-1}$. Defining $R_i$ to be the residue of the numerator in the operation just described ($R_i = RES\{t_i - n_{i-1}\}$), we have:

$$FP\{t_i - n_{i-1}\} = \frac{R_i}{S - D_i - \frac{1}{2}} \quad (9)$$

Combining this result with Equation (6b), we have:

$$R_i = (t_i - n_i)\,(S - D_i - ½) \quad (10)$$

Since $n_{i-1}$ will have been generated from $n_{i-2}$ by an equivalent division process, the residue $R_{i-1}$ from that division must be:

$$R_{i-1} = (t_{i-1} - n_{i-1})\,(S - D_{i-1} - ½) \quad (11)$$

Thus, substituting Equation (11) into Equation (8), we obtain:

$$t_i - n_{i-1} = \frac{n_{i-1} - \frac{2}{k} D_i + R_{i-1}}{S - D_i - \frac{1}{2}} \quad (12)$$

Equations (6a) and (12), the definition of $D_i$, and the discussion of division by repeated subtraction yield the following recursion rules for obtaining $n_i$, $R_i$, and $D_i$ from their predecessors:

$$D_i = D_{i-1} + 1 \quad (13a)$$

$$n_i = n_{i-1} + GI\left\{ \frac{n_{i-1} - \frac{2}{k} D_i + R_{i-1}}{S - D_i - \frac{1}{2}} \right\} \quad (13b)$$

$$R_i = RES\left\{ \frac{n_{i-1} - \frac{2}{k} D_i + R_{i-1}}{S - D_i - \frac{1}{2}} \right\} \quad (13c)$$

This recursive algorithm, starting from suitably chosen initial values of n, R, and D, generates the required sequence $n_1, n_2, \ldots$ of times at which the delay must be incremented (i.e., the delay controller 24$_i$ must emit a STALL signal).

A hardware embodiment of the recursion in Equation (13) is based on repeated subtraction, as in the discussion of Equation (8). In principle such a hardware embodiment calculates $n_i$ from $n_{i-1}$ as follows.

At $n=n_{i-1}$, a register N is loaded with the numerator in Equation (13b), and a second register A is loaded with the denominator. At $n=n_{i-1}+1$, A is subtracted from N. At $n=n_{i-1}+2$, a second such subtraction occurs. Each subtraction consumes one sampling-clock period. This process repeats until N<A. At that time, the number of sampling-clock periods consumed is equal to $n_i - n_{i-1}$, in accordance with Equation (13b), so $n=n_i$. At the same time, the quantity remaining in N is $R_i$, in accordance with Equation (13c). Since $n=n_i$, the delay controller 24$_i$ outputs a STALL signal (causing D to be incremented from $D_i$ to $D_{i+1}$). The calculation of $n_i$ is complete, and registers N and A must be prepared for the calculation of $n_{i+1}$.

In practice, the following modifications of this process are necessary:

1. The loading of register N with the numerator of Equation (13b) must be combined in a single sampling-clock period with the first subtraction of A from N. This combined result is loaded into N when $n=n_{i-1}+1$.
2. Another register, B, is needed to prepare the quantity to be loaded into N at the beginning of each calculation cycle.

In addition, one more modification is expedient:

3. The contents of A are made equal to the negative of the denominator in Equation (13b), so that A can be added to rather than subtracted from N. The condition for incrementing D thus becomes N+A<0.

From Equation (13) and point 1 above, the quantity which must be loaded into register N at $n=n_{i-1}+1$ is:

$$\left(n_{i-1} - \frac{2}{k} D_i + R_{i-1}\right) - \left(S - D_i - \frac{1}{2}\right) = R_{i-1} + \left[\frac{1}{2} + \left(1 - \frac{2}{k}\right) D_i + n_{i-1} - S\right] \quad (14)$$

At $n=n_{i-1}$, N contains $R_{i-1}$, so the bracketed quantity in Equation (14) must be added to N at $n=n_{i-1}+1$. This is the quantity to be supplied by register B. Register B's value is generated by a recursive process. From Equation (14), the change in B from $n=n_{i-1}$ to $n_i$ is:

$$\Delta B = (n_i - n_{i-1}) + (1 - 2/k) \quad (15)$$

Thus, after appropriate initialization, B can be made to have the correct value at each $n_i$ by incrementing B at each sampling clock, and, in addition, adding (1−2/k) to B each time D is updated.

Register A is constant between D updates; the change in A from $n=n_{i-1}$ to $n=n_i$ is:

$$\Delta A = +[-(S-D_i-\tfrac{1}{2})]-[-(S-D_{i-1}-\tfrac{1}{2})]=1 \qquad (16)$$

Thus A must be incremented by 1 each time D is updated. The contents of registers A, B and N can be summarized as follows; at $n=n_{i-1}$, $$A=-(S-D_{i-1}-\tfrac{1}{2}) \qquad (17a)$$

$$B=n_{i-1}+\tfrac{1}{2}-S+(1-2/k)D_i \qquad (17b)$$

$$N=R_{i-1} \qquad (17c)$$

The recursion rules for A, B, D, and N developed above can be summarized as follows:

If N+A≧0 (no D update):

$$N \leftarrow N+A \qquad (18a)$$

$$A \leftarrow A \qquad (18b)$$

$$B \leftarrow B+1 \qquad (18c)$$

$$D \leftarrow D \qquad (18d)$$

If N+A<0 (D update required):

$$N \leftarrow N+B \qquad (19a)$$

$$A \leftarrow A+1 \qquad (19b)$$

$$B \leftarrow B+(2-2/k) \qquad (19c)$$

$$D \leftarrow D+1 \text{ [emit a STALL signal]} \qquad (19d)$$

The "D update required" condition occurs when $n=n_i$ for any i; the "no D update" condition occurs for all other values of n.

Figure 9:
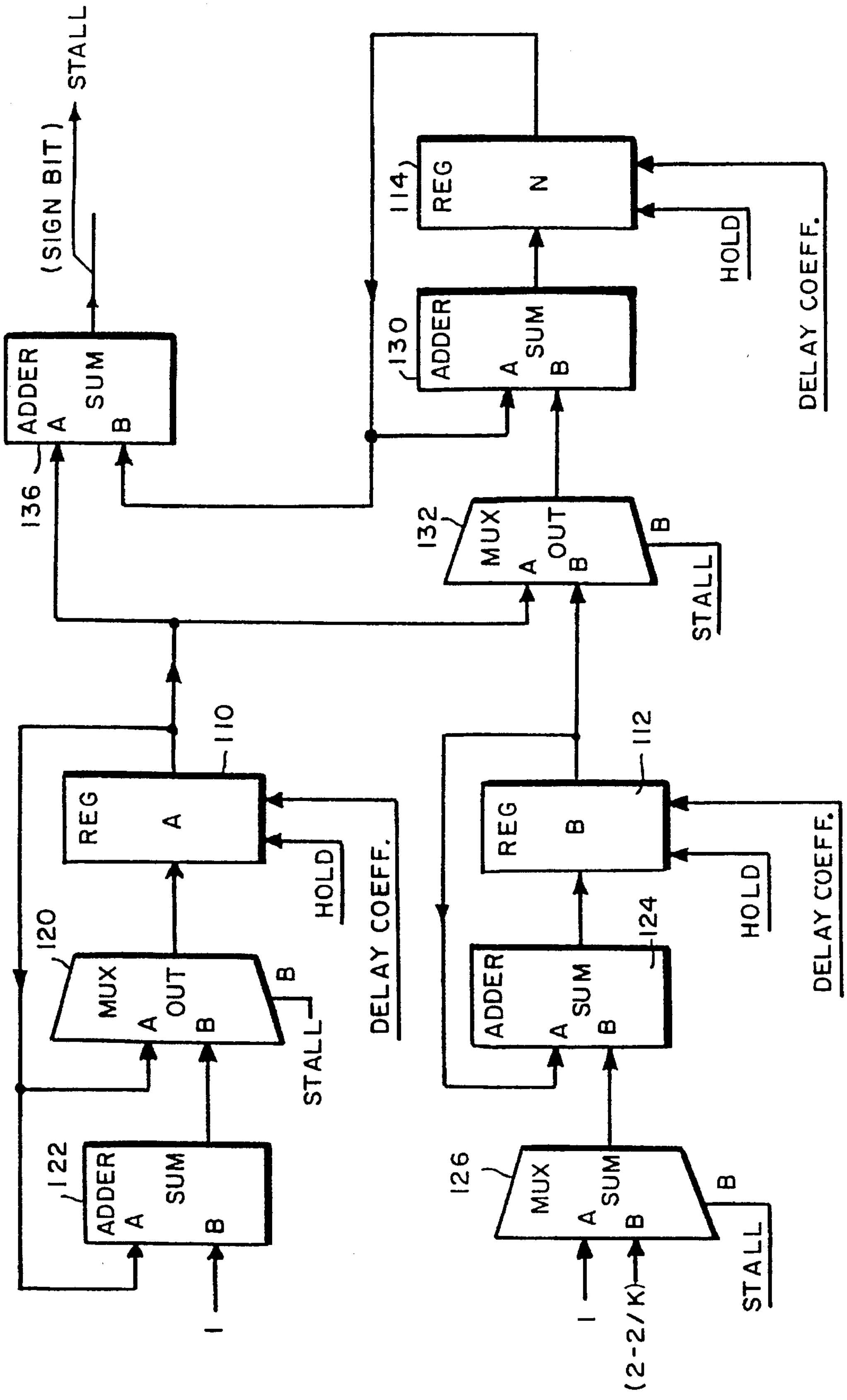
FIG. 9 is a block diagram of a first embodiment of the delay controller in accordance with the present invention.

The recursion rules in Equations (18) and (19) are embodied directly in the circuit shown in block diagram form in FIG. 9. The circuit includes a register 110 which holds the quantity A, a register 112 which holds the quantity B and a register 114 which holds the quantity N. Each register is clocked by the sampling clock. Adder 136 generates a signal equal to N+A. The sign bit of this signal, which has the logical value (N+A) <0, is the STALL signal. Thus, STALL=TRUE indicates that the Equation (19) update rules should be used; STALL=FALSE indicates that the Equation (18) rules should be used. In addition, the STALL signal is sent to the delay unit $\mathbf{22}_i$ where it causes the delay D to be incremented.

A multiplexer 120 supplies inputs to register 110 on each clock pulse. The multiplexer 120 is controlled by the STALL signal. When the STALL signal is true, the multiplexer 120 supplies the output of an adder 122 to the register 110. The adder 122 adds 1 to the output of register 110. When the STALL signal is false, the multiplexer 120 supplies the output of register 110 to its input.

The register 112 receives inputs on each clock pulse from an adder 124, which sums the output of register 112 and the output of a multiplexer 126. The multiplexer 126 is controlled by the STALL signal. When the STALL signal is true, the multiplexer 126 supplies the value (2–2/k) to one input of adder 124. When the STALL signal is false, the multiplexer 126 supplies the value 1 to adder 124.

The register 114 receives inputs from an adder 130 on each clock pulse. The adder 130 sums the output of the register 114 and the output of a multiplexer 132. The multiplexer 132 is controlled by the STALL signal. When the STALL signal is true, the multiplexer 132 supplies the output of register 112 to one input of adder 130. When the STALL signal is false, the multiplexer 132 supplies the output of register 110 to adder 130. An adder 136 sums the outputs of registers 110 and 114 and outputs the STALL signal.

The registers 110, 112 and 114 receive appropriate bits of the delay coefficients which contain the initial values of A, B and N for a given steering angle. The registers 110, 112 and 114 also receive a Hold signal. When the Hold signal is active, the clock has no effect on the registers. The hold function is utilized to inhibit the operation of the delay controller until signals corresponding to a predetermined minimum image depth are being received.

Figure 10:
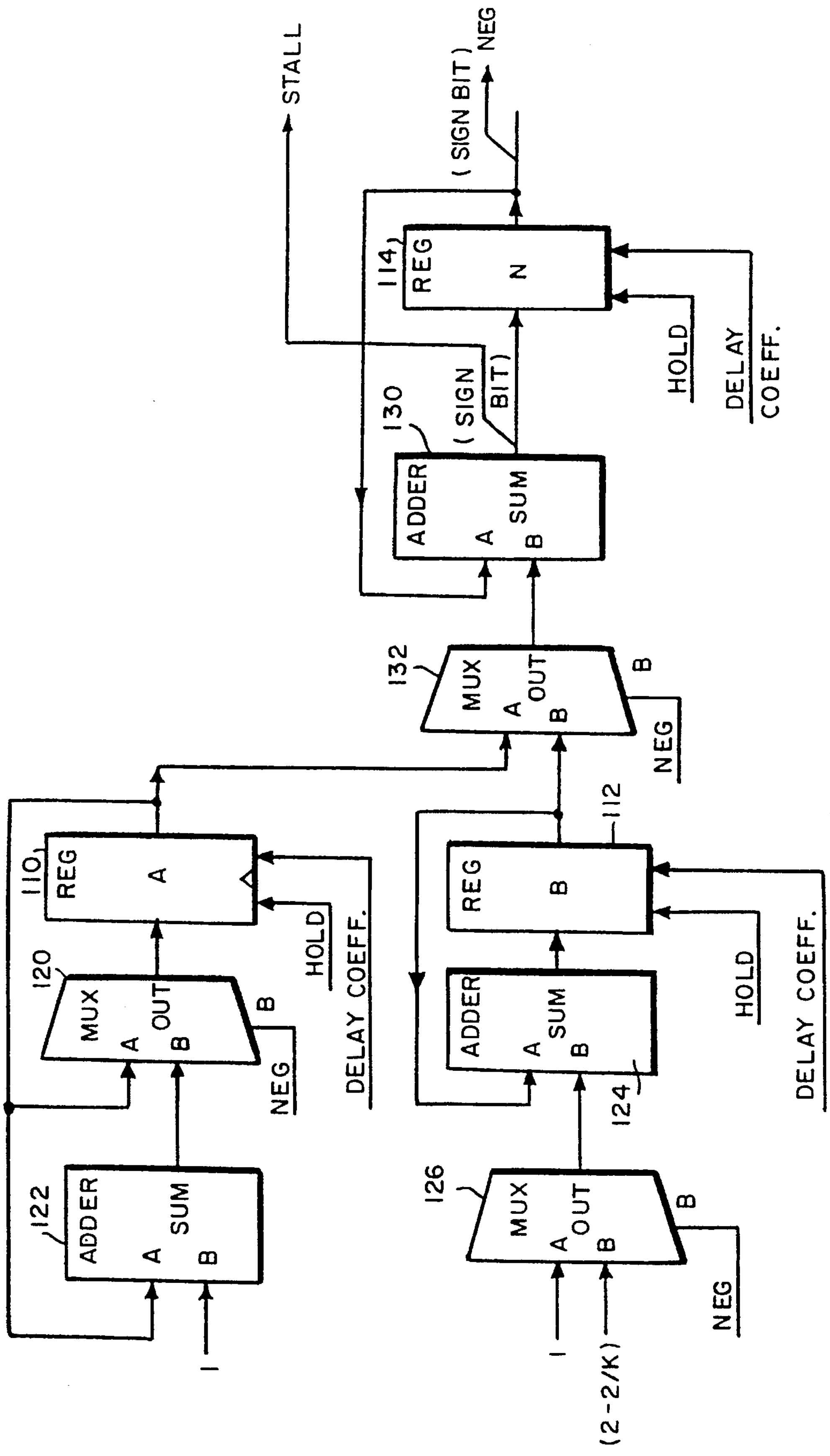
FIG. 10 is a block diagram of a second embodiment of the delay controller in accordance with the present invention.

The delay controller shown in FIG. 9 can be simplified by delaying the Equation (18) vs (19) update decision by one sampling clock. This second, simplified embodiment of the delay controller is shown in FIG. 10. The value in the N register 114 is allowed to become negative, and its sign (here labeled NEG) replaces STALL as the update-rule-selection control signal for A, B, and N. STALL itself, which now controls only the D update (in the delay unit), equals the sign of the output of adder 130. As shown in FIG. 10, the logical value of STALL in this embodiment of the delay controller is:

$$\text{STALL} \quad = (N+A) < 0 \text{ if NEG} = \text{FALSE}$$
$$\qquad\qquad = (N+B) < 0 \text{ if NEG} = \text{TRUE}$$

The update rules embodied in this embodiment of the delay controller are:

If STALL=FALSE $$D \leftarrow D \text{ (no update)} \qquad (20)$$

If STALL=TRUE $$D \leftarrow D+1 \text{ (D update required)} \qquad (21)$$

If N≧0

$$N \leftarrow N+A \qquad (22a)$$

$$A \leftarrow A \qquad (22b)$$

$$B \leftarrow B+1 \qquad (22c)$$

If N<0

$$N \leftarrow N+B \qquad (23a)$$

$$A \leftarrow A+1 \qquad (23b)$$

$$B \leftarrow B+(2-2/k) \qquad (23c)$$

This second delay controller embodiment produces exactly the same sequence of STALL signals as the one shown in FIG. 9.

The delay controller described above has been shown to implement the ideal-delay Equation (4) exactly, within the elapsed-time and delay quantization limits. To achieve this exact solution, the values in the A, B, and N registers must be of infinite precision. In practice, a finite number of bits must be used. A fractional part of 3 bits (resolution of ⅛) has been found to assure maximum errors much smaller than the delay quantum. Thus in a preferred embodiment of the delay controller, the number of fractional bits is three in each register 110, 112 and 114.

The length of the integer part of the A, B, and N registers depends on maximum probe size (aperture length), wavelength, maximum steering angle, minimum focal distance of interest, and sampling-clock period. In a preferred embodiment, which encompasses many cases of practical interest, the lengths are:

A: 10 bits (integer)+3 bits (fraction)+1 bit (sign)=14 bits total

B: 14 bits (integer)+3 bits (fraction)=17 bits total

N: 14 bits (integer)+3 bits (fraction)+1 bit (sign)=18 bits total

If k=1, this delay controller is capable of operation for all n>0. For k>1, there exists minimum value of n, $n_{min}$, (dependent on X and S) below which the controller cannot function correctly. For values of $n>n_{min}$, the delay controller gives the correct, non-approximate solution (within the error limits set by finite register resolution). This limit on minimum n is imposed by the method chosen for controlling D: since STALL is only available once per sampling-clock period, then the maximum change in D is one delay quantum per sampling-clock period. For large X and S and k>1, this rate is exceeded for small n.

In a practical imaging system based on this delay controller, with k>1, a fixed focus can be used for $n<n_{min}$ and dynamic focus used for larger n. For small n, only transducer elements near the center of the transducer (having small X and S) are useful due to other effects, so in many cases the limit imposed by the delay controller is not of practical significance. For small n, only a small part of the transducer ("active aperture") is used to form the image, and the active aperture is expanded as n grows, until all elements are in use. This expanding-aperture technique is widely used in existing ultrasound imaging systems.

The delay controllers shown in FIGS. 9 and 10 and described above generate delays for a steering angle Θ that is constant during reception of ultrasound energy along each scan line. In some cases, it may be desirable to vary the steering angle Θ dynamically during reception of ultrasound energy, in addition to dynamic focusing as described above. The steering angle Θ of the receive scan line is varied by a deviation ΔΘ, which is a function of time, during reception of ultrasound energy. As a result, the receive scan line, or scan path, may not be a straight line. As used herein, the term "warping" refers to dynamically varying the steering angle Θ by a deviation ΔΘ during reception of ultrasound energy. As described below, the deviation ΔΘ is controlled by varying the delays applied to the received signals in each channel of the beamformer.

Equation (2) above gives the round trip travel time $T_i$ for element $E_i$ of the transducer array. In order to obtain the round trip time for a small deviation in the steering angle, Θ+ΔΘ is substituted for Θ in Equation (2). Using the small angle approximations sin ΔΘ approximately equal ΔΘ and cos ΔΘ approximately equal 1, we obtain $$T_i = t/2 + \left[ \left( \frac{t}{2} \right)^2 - (x_i(\sin\theta + \Delta\theta\cos\theta) + y_i(\cos\theta - \Delta\theta\sin\theta)) \frac{t}{c} + \frac{x_i^2 + y_i^2}{c^2} \right]^{1/2} \quad (24)$$

For a flat array, $y_i=0$, and the round trip travel time $T_i$ is $$T_i = t/2 + \left[ \left( \frac{t}{2} \right)^2 - x_i(\sin\theta + \Delta\theta\cos\theta) \frac{t}{c} + \frac{x_i^2}{c^2} \right]^{1/2} \quad (25)$$

Equation (25) has the same form and dependence on t as Equation (24). If we can find a solution for Equation (20), we can solve Equation (24) by substituting:

$$x_i(\sin\theta+\Delta\theta\cos\theta) \rightarrow x_i(\sin\theta+\Delta\theta\cos\theta)+y_i(\cos\theta-\Delta\theta\sin\theta) \quad (26a)$$

$$x_i^2 \rightarrow x_i^2+y_i^2 \quad (26b)$$

Therefore, we will base the following discussion on Equation (25).

A comparison of Equation (25) with Equation (2) for the case where $y_i=0$ indicates that Equation (25) is identical to Equation (2) with the substitution $$\sin\theta \rightarrow \sin\theta+\Delta\theta\cos\theta \quad (27)$$

The above derivation can be used to determine the contents of registers A (110), B (112), and N (114) (FIGS. 9 and 10) for the delay generator with warping in terms of the contents of the registers A, B and N in the delay generator without warping. The delay generator with warping is one in which the steering angle Θ can be varied dynamically by a small deviation ΔΘ during reception of ultrasound energy, as described above. By making the substitution of Equation (27) in Equations (17a), (17b) and (17c) for A, B and N, respectively, the following results are obtained.

$$[A]_{warped}=[A]_{nonwarped}-\Delta\theta\cos\theta x_i \quad (28)$$

$$[B]_{warped}=[B]_{nonwarped}-\Delta\theta\cos\theta x_i \quad (29)$$

$$[N]_{warped}=[N]_{nonwarped} \quad (30)$$

where $x_i$ is in units of $C\tau_o$.

Since the same term (ΔΘcos Θe) is subtracted from the A register and from the B register, it may be equivalently subtracted from the N register. Thus, the operation of the warped delay generator is based on the operation of the non-warped delay generator described above, with ΔΘcos Θe subtracted from the N register.

The desired values of steering angle deviation ΔΘ to control the delay generator with warping are received from the controller 28 (FIG. 1). The values of steering angle deviation ΔΘ vary with depth as a function of time during reception and also vary with transmit focal depth, steering angle and transducer element position. The ΔΘ values are stored and then are supplied to each channel of the beamformer on a dynamic basis during imaging. In order to keep the data storage and handling requirements within practical limits, the region being imaged is preferably divided into zones. Each zone is defined by start depth and a stop depth from the transducer array. Within each zone, a constant value of ΔΘ is utilized. In a preferred embodiment, the region being imaged is divided into 16 zones. In zone 0, closest to the transducer array, ΔΘ is arbitrarily set at 0. The value of ΔΘ in zone 15 is used for all depths greater than zone 15.

The delay generator with warping is implemented as a modification of the delay generator without warping. As described above, warping can be implemented by subtracting the value of ΔΘcos Θe from the N register in the delay controller **24*i*** of each channel. The calculation is performed on a zone-by-zone basis so that the value of ΔΘ for the following zone is correct at the end of each zone. The times when the STALL commands are issued are modified by the $\Delta\Theta$ values to result in warping of each receive scan line. As a further simplification, the calculation of $\Delta\Theta$ for each zone is preferably performed for groups of eight beamformer channels, and the same $\Delta\Theta$ values are used by the eight channels in each group.

Changing the N register instantaneously by $\Delta\Theta\cos\Theta e$ does not instantaneously change the scan angle by $\Delta\Theta$. To change the scan angle at any point in the line, all the changes muse be added to the N register that would have occurred if the angle had been changed at the beginning of the line. Consider the case where the scan angle changes at the end of each focal zone and we want the scan path to have the correct angle at the end of the zone. From Table 1 below, we see that to change the scan angle from $\Delta\Theta_1$ to $\Delta\Theta_2$ during zone 2, we must use the angle $\Delta\Theta_1+3(\Delta\Theta_2-\Delta\Theta_1)$ because we are making the change during one zone instead of three zones from the start of the line.

TABLE 1

| Zone | Deviation $\Delta\Theta$ | Required change during zone |
|---|---|---|
| 0 | $\Delta\Theta_0$ | $\Delta\Theta_1$ |
| 1 | $\Delta\Theta_1$ | $\Theta_0 + 2(\Delta\Theta_1 - \Delta\Theta_0)$ |
| 2 | $\Delta\Theta_2$ | $\Delta\Theta_1 + 3(\Delta\Theta_2 - \Delta\Theta_1)$ |
| 3 | $\Delta\Theta_3$ | $\Delta\Theta_2 + 4(\Delta\Theta_3 - \Delta\Theta_2)$ |
| . | . | . |
| . | . | . |
| . | . | . |

In general, a change of Z+1 times the difference in the start and end zone angles is applied in zone Z.

The above scheme gives exactly the desired changes at the end of the focal zones. At any point along the scan line, the effective deviation angle $\gamma(t)$, is given by $$\gamma(t) = \frac{1}{t}\int_0^t \Delta\theta(t)dt \tag{31}$$

Integrating up to zone Z gives $$\gamma(t) = \frac{1}{t}\left[\Delta\theta_{Z-1}ZT + \int_{ZT}^{T}(\Delta\theta_{Z-1} + (Z+1)(\Delta\theta_Z - \Delta\theta_{Z-1}))dt\right] \tag{32}$$

where T is the time duration of a focal zone. Finishing the integration yields $$\gamma(t) = \frac{1}{t}\left[\Delta\theta_{Z-1}ZT + (\Delta\theta_{Z-1} + (Z+1)(\Delta\theta_Z - \Delta\theta_{Z-1}))(t-ZT)\right] \tag{33}$$

Changing the origin of time from the start of the line to the start of zone Z gives $$\gamma(t) = \frac{1}{ZT+1}\left[\Delta\theta_{Z-1}ZT + (\Delta\theta_{Z-1} + (Z+1)(\Delta\theta_Z - \Delta\theta_{Z-1}))t\right] \tag{34}$$

The above equation shows that the scan path between zone ends is not a straight line. Simulations show that the scan angle changes faster at the start of a zone than at the end. The exact path does not matter. The important feature is that the delay generator keeps all the channels focused.

Figures 1, 11:
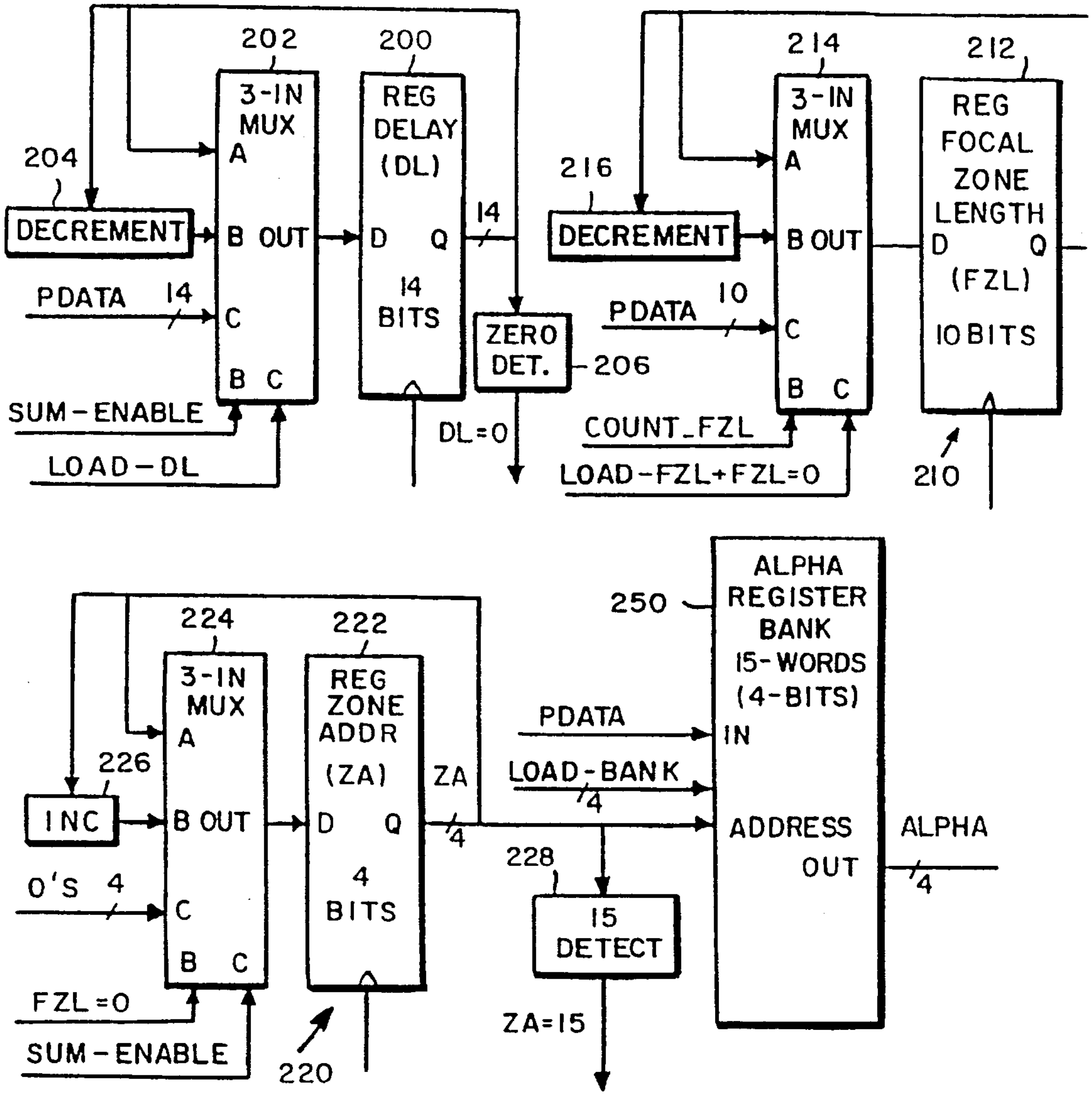
Figures 2, 11:
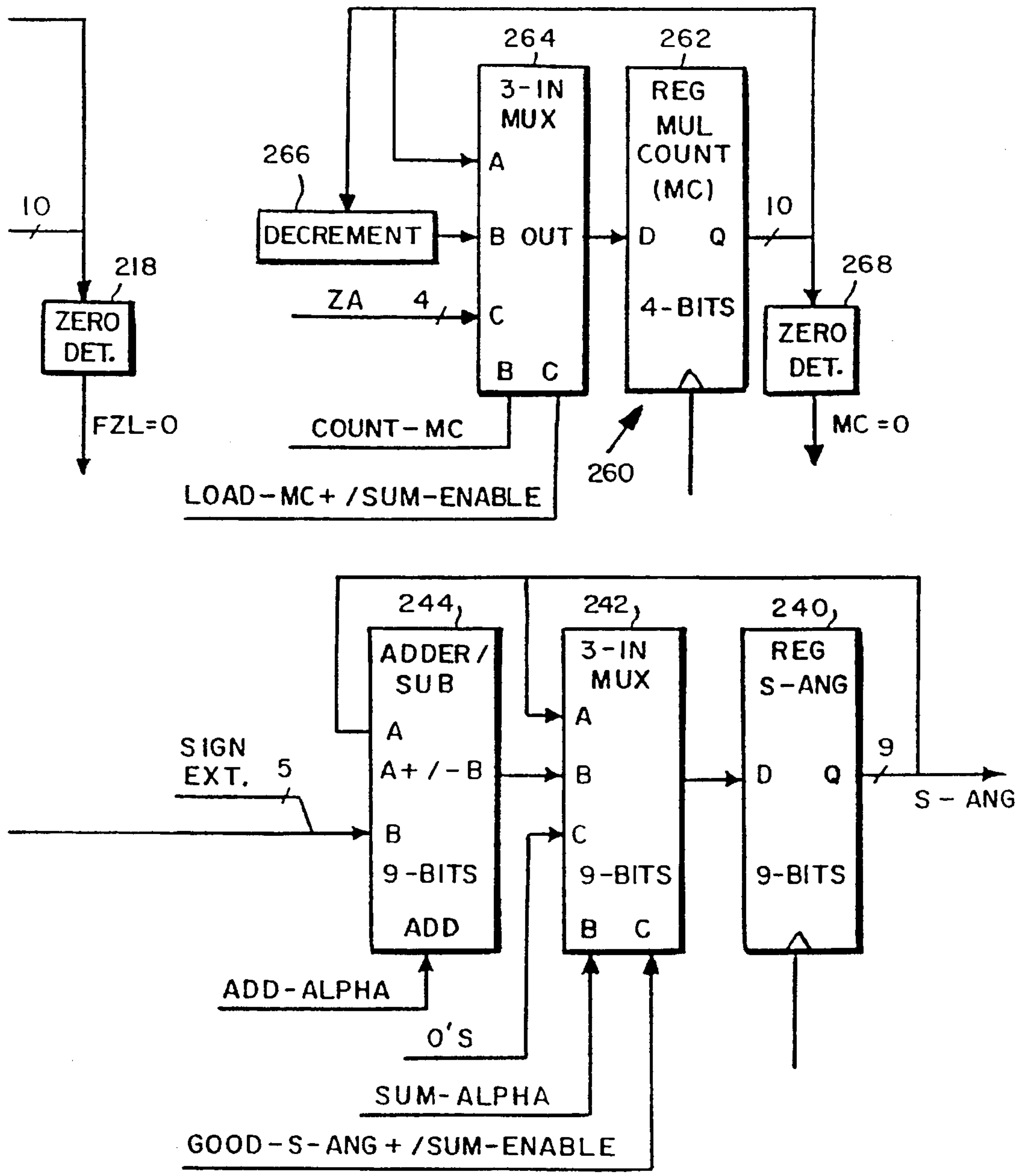
Figures 1, 12:
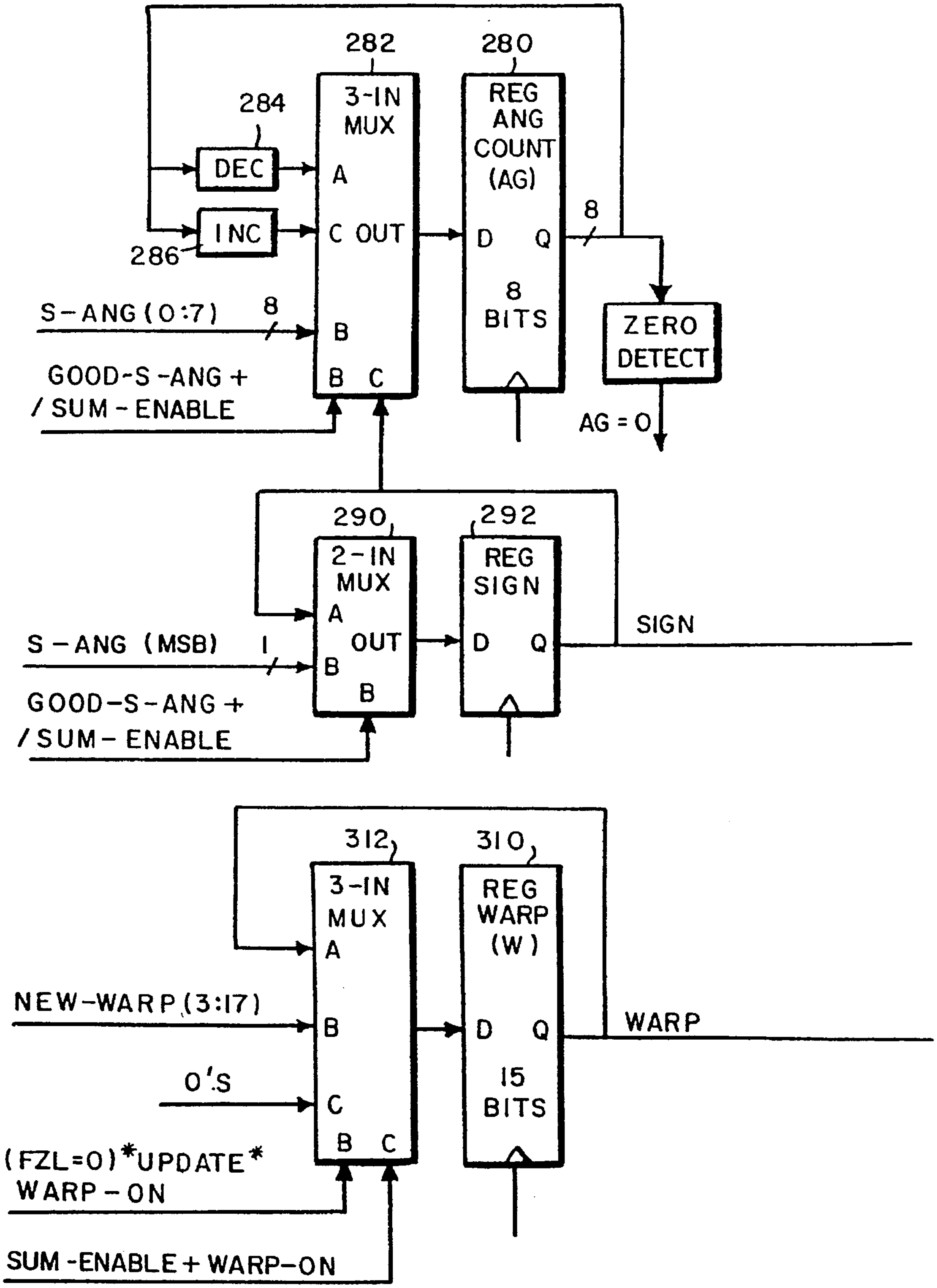
Figure 12:
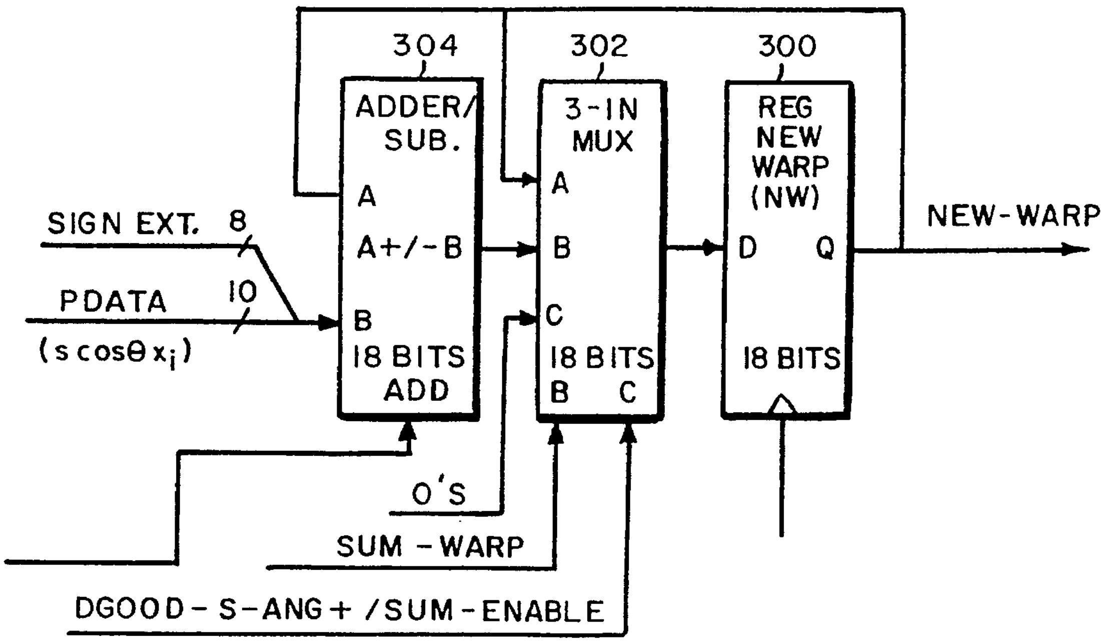
Figure 2:
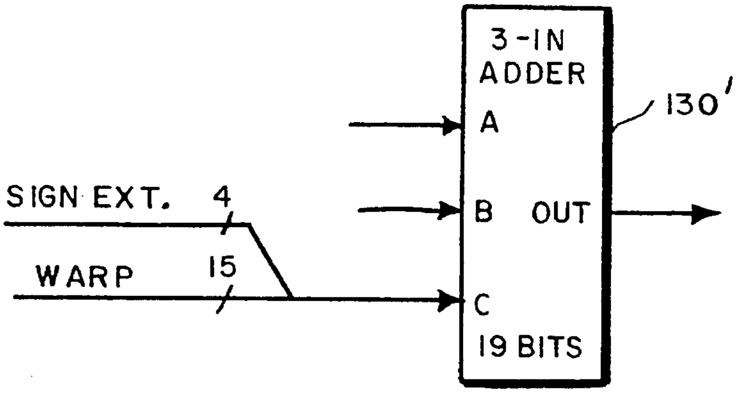

Since simulations indicate that 16 zones of warping are adequate, the warped scan path can be specified by 15 numbers. Each number specifies the amount of warping at the end of the zone. To simplify the hardware and software, the amount of warp at the end of zone 0 is 0, and the warp after zone 15 is the same as at the end of zone 15. Simulations also show that the warp angle can be specified by a 4 bit 2's complement number. Without loss of any desired scan modes, groups of eight channels can share a common scan path specification. FIGS. 11-1 and 11-2 show the hardware which groups of eight channels can share, and FIGS. 12-1 and 12-2 show the additional hardware which must be added to each delay controller to perform warping. Appendix A contains the hardware control equations. In Appendix A, the symbol ":=" means set equal on the next clock cycle.

Unlike the normal delay generator which is held off until the F number is large enough, the delay generator with warping hardware begins its calculations at time t=0 for the center channel. A delay (DL) register 200 and its associated hardware, including multiplexer 202, decrementer 204 and zero detector 206, form a programmable delay from the rising edge of the SUM-ENABLE signal to t=0. DL register 200 is loaded at the start of each line.

A focal zone length (FZL) register 212 and its associated hardware, including multiplexer 214, decrementer 216 and zero detector 218, provide variable length focal zones. Zero detect circuitry 218 provides a pulse at the end of each zone. These pulses are counted by a zone address (ZA) counter 220, which includes ZA register 222, multiplexer 224, incrementer 226 and 15 detector 228. The FZL register 212 is loaded at the start of each line and at the end of each zone. The ZA register 222 is cleared at the start of each line.

The delay generator with warping calculates the warp as $$warp=-(\Delta\theta_{Z-1}-(Z+1)\ (\Delta\theta_Z-\Delta\theta_{Z-1}))x_i\cos\theta \tag{35}$$

Expressing the warp angle as an integer times a scale factor, s, gives $$warp=-(alpha_{Z-1}-(Z+1)\ (alpha_Z-alpha_{Z-1}))\ (s\ \cos\theta x_i) \tag{36}$$

where alpha ranges from −7 to +7. $Alpha_1$ is stored in alpha[0], location 0 of alpha register bank 250. Table 2 below shows the value of the alpha factors in the warp equation for each zone.

TABLE 2

| ZONE | ALPHA FACTOR |
|---|---|
| 0 | 0 |
| 1 | 2*alpha[0] |
| 2 | alpha[0] + 3*(alpha[1] − alpha[0]) |
| 3 | alpha[1] + 4*(alpha[2] − alpha[1]) |
| 4 | alpha[2] + 5*(alpha[3] − alpha[2]) |
| 5 | alpha[3] + 6*(alpha[4] − alpha[3]) |
| 6 | alpha[4] + 7*(alpha[5] − alpha[4]) |
| . . . | |
| 15 | alpha[13] + 16*(alpha[14] − alpha[13]) |
| 16 | alpha(14] |

Figures 1, 13:
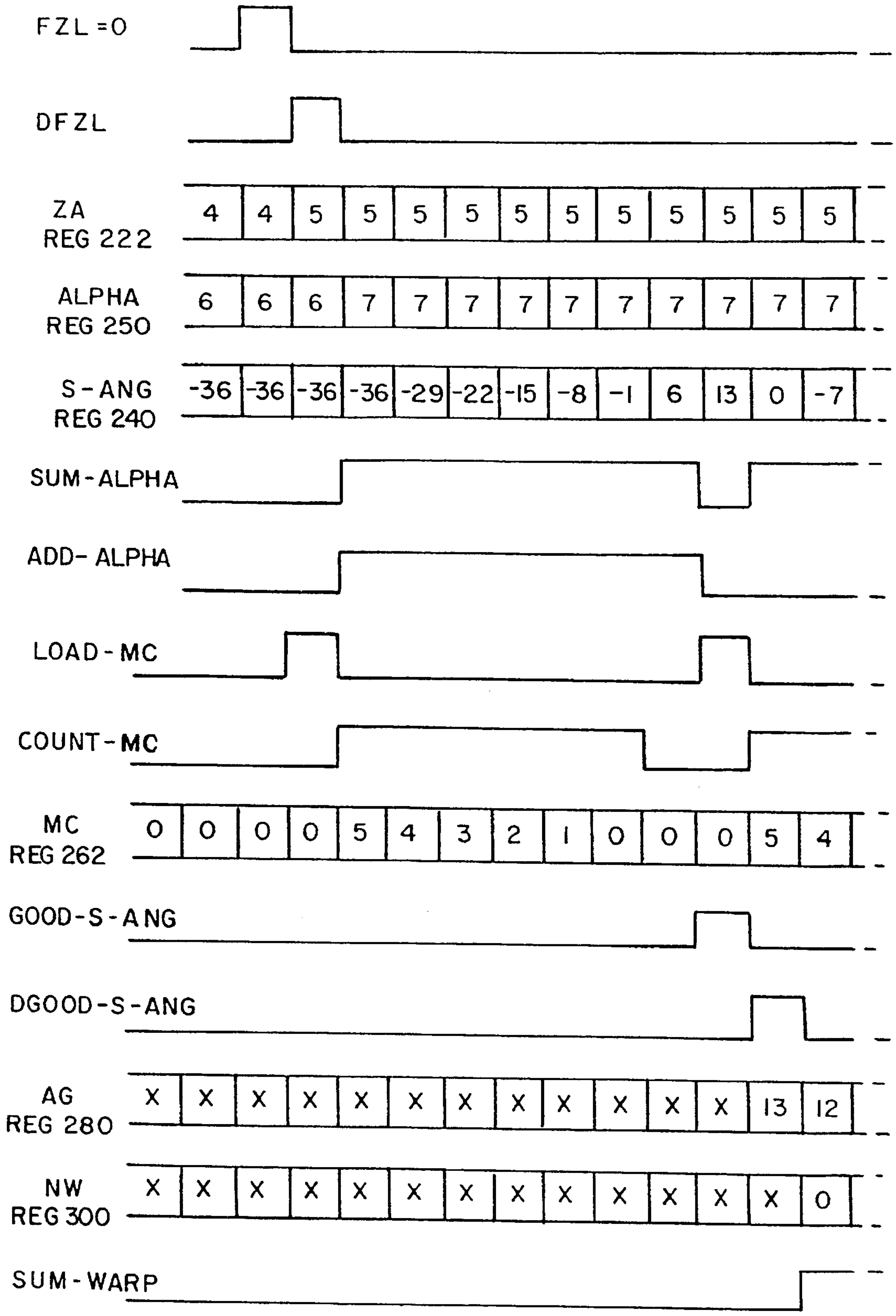
Figures 2, 13:
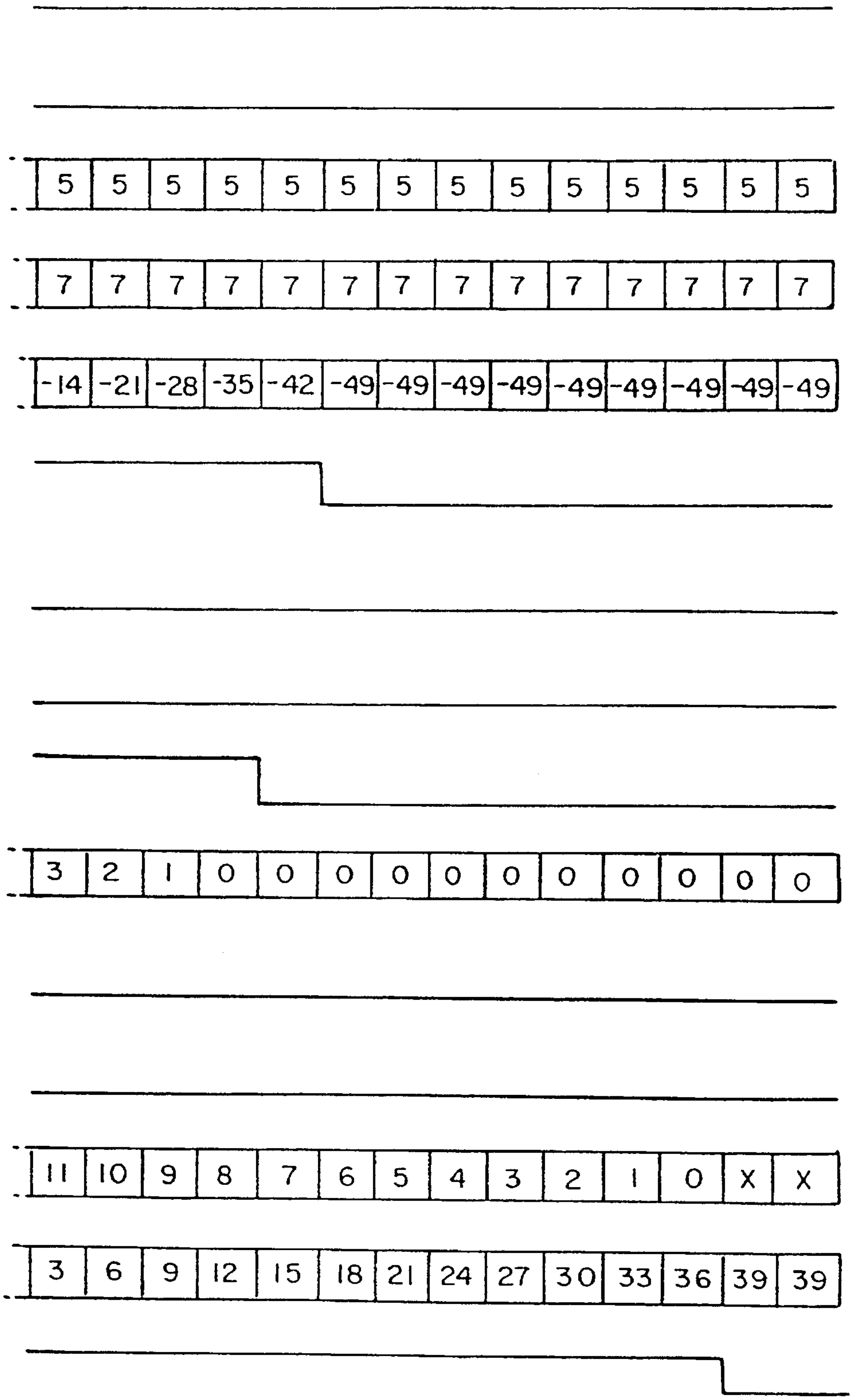

FIGS. 13-1 and 13-2 show the timing for the calculation of the zone 6 alpha factor assuming alpha[4]=6 and alpha [5]=7. Since the calculation must be complete at the start of zone 6, it is performed during zone 5. In FIGS. 13-1 and 13-2, the contents of the indicated registers are shown during each clock cycle. Associated with an S-ANG register 240 are a multiplexer 242 and an adder/subtractor 244. At the start of zone 5, the S-ANG register 240 contains −6*alpha[4]=−36 and the FZL counter 210 generates a pulse. After the pulse increments the ZA counter 220, alpha[5] becomes available at the output of the alpha register bank 250. The contents of the ZA register 222 are clocked into mul count (MC) register 262. Under control of MC counter 260, which includes MC register 262, multiplexer 264, decrementer 266 and zero detector 268, the output of the register bank 250 adds to the S-ANG register 240 for 7 cycles. The S-ANG register 240 now contains 7*alpha[5]–6*alpha[4]=13. The GOOD-S-ANG signal then loads this result into an angle count (AG) register 280 (FIG. 12-1), and a SIGN register 292. Associated with AG register 280 are multiplexer 282, decrementer 284, incrementer 286 and zero detector 288, and associated with SIGN register 292 is multiplexer 290. The MC register 262 is reloaded and the S-ANG register 240 is cleared. Under control of the MC counter 262, the output of the register bank 250 now subtracts from the S-ANG register 240 for 7 cycles. The S-ANG register 240 now contains –7alpha[5]=49.

By repetitive addition in the per channel hardware, $x_i$ cos Θs is multiplied by –(7*alpha[5]–6*alpha[4]). The angle count register 280 serves as the count register, and a new warp (NW) register 300 serves as the accumulator. A multiplexer 302 and an adder/subtractor 304 are associated with NW register 300. The $x_i$ cos Θs term has 3 more bits of precision than the other delay generator presets to reduce the magnification of truncation error generated by repetitive addition. The extra precision is removed in rest of the calculations by loading a warp (W) register 310 with only the top 15 bits of the final NW register 300 results. A multiplexer 312 is associated with the W register 310.

As a final item of interest, the delay generator with warping accesses alpha[14] during the 15th zone and calculates the alpha factor, 17*alpha[14]–16*alpha[14]=alpha [14]. This value is then used for the rest of the scan line.

To implement the delay generator with warping, the per channel hardware shown in FIGS. 12-1 and 12-2 is added to the per channel hardware shown in FIG. 9 or FIG. 10. The two input adder 130 shown in FIGS. 9 and 10 is replaced with a three input adder 130' shown in FIG. 12-2. The common hardware shown in FIGS. 11-1 and 11-2 is replicated for each group of 8 channels.

In one example of the delay generator with warping, the DL register 200 has 14 bits, the FZL register 212 has 10 bits, the MC register 262 and the ZA register 222 each have 4 bits, the alpha register bank 250 has 15 words by 4 bits, and the S-ANG register 240 has 9 bits. In the per channel additional hardware, the AG register 280 has 8 bits, the NW register 300 has 18 bits and the W register 310 has 15 bits. It will be understood that different register sizes can be used, depending on the system requirements and the required precision.

The presets provided by the controller 28 to the common warp generator hardware shown in FIG. 11 include the alpha values for the alpha register bank 250 (15 words by 4 bits), the required delay for DL register 200 (14 bits) and the focal zone length for FZL register 212 (10 bits). The preset for the additional per channel hardware shown in FIGS. 12-1 and 12-2 includes the contents of NW register 300 (10 bits). The external control signals for the delay generator with warping are as follows:

(1) SUM-ENABLE is a timing signal which enables the start of the delay generator with warping;

(2) LOAD-DL is a control pulse to load the delay register 200 before the start of a line;

(3) LOAD-FZL is a control pulse to load the FZL register 212 before the start of the line;

(4) LOAD-BANK is a control bus to load the alpha register bank 250 before the start of the line;

(5) WARP-ON is a control bit that enables warping; and (6) PDATA is a data bus for loading registers.

While there have been shown and described what are at present considered the preferred embodiments of the present invention, it will be obvious to those skilled in the art that various changes and modifications may be made therein without departing from the scope of the invention as defined by the appended claims.

APPENDIX A

CONTROL LOGIC EQUATIONS FOR COMMON WARP GENERATOR HARDWARE

COUNT-FZL:=SUM-ENABLE*(DL=0)+COUNT-FZL*SUM-ENABLE

LATER-DL:=(DL=0)+LATER-DL*SUM-ENABLE

LOAD-MC:=/LATER-DL*(DL=0)+(FZL=0)+ADD-ALPHA*/COUNT-MC

COUNT-MC:=LOAD-MC+SUM-ENABLE*COUNT-MC*/(MC=0)

SUM-ALPHA:=LOAD-MC+SUM-ENABLE*SUM-ALPHA*COUNT-MC

DFZL:=/LATER-DL*(DL=0)+(FZL=0)

ADD-ALPHA:=DFZL+SUM-ENABLE*ADD-ALPHA*COUNT-MC

GOOD-S-ANG:=ADD-ALPHA*/COUNT-MC

DGOOD-S-ANG:=GOOD-S-ANG

SUM-WARP:=DGOOD-S-ANG*/(AG=0)+SUM-ENABLE*SUM-WARP*/(AG=0)

UPDATE:=/LATER-DL*(DL=0)+SUM-ENABLE*UPDATE*/((FZL=0)*(ZA=15))

What is claimed is:

1. In an ultrasound beamformer for processing received signals from an array of transducer elements, each providing a received signal, to form a receive beam, said beamformer comprising a delay generator corresponding to each transducer element for delaying the received signal and a combiner for combining the delayed signals to form said receive beam, each delay generator comprising:

a delay unit for delaying the received signal by a quantized delay which is variable in response to a change delay signal, said delay unit comprising a circular memory having locations for storing discrete time values of said received signal, wherein the discrete time values of said received signal are written in successive locations in said memory; and a delay controller for generating said change delay signal at discrete times during reception of ultrasound energy, to steer said receive beam to a selected steering angle and to dynamically focus said receive beam, said change delay signal controlling reading of the discrete time values of said received signal from locations in said memory corresponding to said quantized delay, said delay controller comprising means responsive to an initial delay value for iteratively generating said change delay signal at each of said discrete times such that said quantized delay is an exact solution, within the quantization error of said delay unit, to the equation for said delay at a given steering angle, transducer element and focal depth at each of said discrete times.

2. A delay generator as defined in claim 1 wherein said delay controller includes means for generating said change delay signal in binary form such that an active state of said change delay signal causes said quantized delay to change by one delay quantum.

3. A delay generator as defined in claim 1 wherein said delay controller includes a plurality of registers for storing values representative of a delay curve for the selected steering angle and means for updating said registers at said discrete times during reception of ultrasound energy, said change delay signal being generated each time the values in said registers meet a predetermined condition.

4. A delay generator as defined in claim 3 wherein said registers include an A register, a B register and an N register, which are updated at said discrete times in accordance with the following rules:

If $N+A \geqq 0$:

$$N \leftarrow N+A$$

$$A \leftarrow A$$

$$B \leftarrow B+1;$$

If $N+A<0$:

$$N \leftarrow N+B$$

$$A \leftarrow A+1$$

$$B \leftarrow B+(2-2/k)$$

where k is the ratio of the interval between said discrete update times and said delay quantum, and wherein the predetermined condition for generating said change delay signal is:

$$N+A<0.$$

5. A delay generator as defined in claim 3 wherein said registers include an A register, a B register, and an N register, which are updated at said discrete times in accordance with the following rules:

If $N \geqq 0$:

$$N \leftarrow N+A$$

$$A \leftarrow A$$

$$B \leftarrow B+1;$$

If $N<0$:

$$N \leftarrow N+B$$

$$A \leftarrow A+1$$

$$B \leftarrow B+(2-2/k)$$

where k is the ratio of the interval between said discrete update times and said delay quantum, and wherein the predetermined condition for generating said change delay signal is:

$$[(N \geqq 0) \text{ AND } (N+A<0)] \text{ OR}$$

$$[(N<0) \text{ AND } (N+B<0)].$$

6. A delay generator as defined in claim 3 further including means for placing said registers in a hold state until reception of ultrasound energy from a predetermined minimum image depth.

7. A delay generator as defined in claim 1 wherein said delay unit includes means for delaying digital representations of said received signals.

8. A delay generator as defined in claim 1 wherein said delay unit includes means for delaying continuous analog representations of said received signals.

9. A delay generator as defined in claim 1 wherein said delay unit includes means for delaying sampled analog representations of said received signals.

10. In an ultrasound beamformer for processing received signals from an array of transducer elements, each providing a received signal, to form a receive beam, said beamformer comprising a delay generator corresponding to each transducer element for delaying the received signal and a combiner for combining the delayed signals to form said receive beam, each delay generator comprising:

a delay unit for delaying the received signal by a quantized delay which is variable in response to a change delay signal, said delay unit comprising a circular memory having locations for storing discrete time values of said received signal, wherein the discrete time values of said received signal are written in successive locations in said memory; and a delay controller for generating said change delay signal at discrete times during reception of ultrasound energy, to steer said receive beam to a dynamically variable steering angle and to dynamically focus said receive beam during reception of ultrasound energy, said change delay signal controlling reading of the discrete time values of said received signal from locations in said memory corresponding to said quantized delay, said delay controller comprising means responsive to an initial delay value for iteratively generating said change delay signal at each of said discrete times such that said quantized delay is an exact solution to the equation for said delay at a given steering angle, transducer element and focal depth.

11. A delay generator as defined in claim 10 wherein said delay controller includes a plurality of registers for storing values representative of a delay curve for steering said receive beam to said dynamically variable steering angle and for dynamically focusing said receive beam, and means for incrementing said registers at said discrete times during reception of ultrasound energy, said change delay signal being generated each time the values in said registers meet a predetermined condition.

12. A delay generator as defined in claim 11 wherein said registers include an A register, a B register, an N register and a W register, which contain values A, B, N and W respectively, as follows:

If $N \geqq 0$:

$$N \leftarrow N+A+W$$

$$A \leftarrow A$$

$$B \leftarrow B+1;$$

If $N<0$:

$$N \leftarrow N+B+W$$

$$A \leftarrow A+1$$

$$B \leftarrow B+(2-2/k)$$

where k is the ratio of the interval between said discrete update times and said delay quantum, and wherein the predetermined condition for generating said change delay signal is:

$$[(N \geqq 0) \text{ AND } (N+A<0)] \text{ OR}$$

$$[(N<0) \text{ AND } (N+B<0)].$$

13. A delay generator as defined in claim 12 wherein said delay controller receives delay coefficients that establish said required delay, said delay coefficients containing information representative of a selected steering angle $\Theta$ and deviations $\Delta\Theta$ from said selected steering angle, said deviations $\Delta\Theta$ being specified for a predetermined number of zones of a region being imaged.

14. A delay generator as defined in claim 13 wherein said delay controller includes means for causing said receive beam to have a specified deviation $\Delta\Theta_Z$ from the selected steering angle $\Theta$ in each zone Z.

15. A delay generator as defined in claim 10 wherein said delay unit includes means for delaying digital representations of said received signals.

16. A delay generator as defined in claim 10 wherein said delay unit includes means for delaying continuous analog representations of said received signals.

17. A delay generator as defined in claim 10 wherein said delay unit includes means for delaying sampled analog representations of said received signals.

* * * * *